US011041014B2

(12) United States Patent
Sato et al.

(10) Patent No.: US 11,041,014 B2
(45) **Date of Patent: *Jun. 22, 2021**

(54) LACTOFERRIN/ALBUMIN FUSION PROTEIN AND PRODUCTION METHOD THEREFOR

(71) Applicant: S & K BIOPHARMA, INC., Kawasaki (JP)

(72) Inventors: Atsushi Sato, Kanagawa (JP); Shinji Kagaya, Kanagawa (JP)

(73) Assignee: S & K Biopharma, Inc., Kawasaki (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/344,875

(22) PCT Filed: Oct. 27, 2017

(86) PCT No.: PCT/JP2017/038866

§ 371 (c)(1),
(2) Date: Jun. 4, 2019

(87) PCT Pub. No.: WO2018/079702

PCT Pub. Date: May 3, 2018

(65) Prior Publication Data

US 2019/0309049 A1 Oct. 10, 2019

(30) Foreign Application Priority Data

Oct. 28, 2016 (JP) ............................ JP2016-212077
Mar. 9, 2017 (JP) ............................ JP2017-044893

(51) Int. Cl.

| | |
|---|---|
| ***C07K 14/79*** | (2006.01) |
| ***C12N 15/62*** | (2006.01) |
| ***C12N 15/82*** | (2006.01) |
| ***C07K 14/765*** | (2006.01) |
| ***A61P 35/00*** | (2006.01) |
| ***A61K 38/40*** | (2006.01) |
| ***C12N 5/10*** | (2006.01) |
| ***C12P 21/02*** | (2006.01) |
| ***A61P 43/00*** | (2006.01) |
| ***A61P 39/04*** | (2006.01) |
| ***C07K 19/00*** | (2006.01) |
| ***A61K 38/38*** | (2006.01) |
| ***A61P 9/10*** | (2006.01) |
| ***C12N 15/09*** | (2006.01) |
| ***A01K 67/027*** | (2006.01) |

(52) U.S. Cl.

CPC .......... *C07K 14/765* (2013.01); *A01K 67/027* (2013.01); *A61K 38/38* (2013.01); *A61K 38/40* (2013.01); *A61P 9/10* (2018.01); *A61P 35/00* (2018.01); *A61P 39/04* (2018.01); *A61P 43/00* (2018.01); *C07K 14/79* (2013.01); *C07K 19/00* (2013.01); *C12N 5/10* (2013.01); *C12N 15/09* (2013.01); *C12P 21/02* (2013.01); *C07K 2319/31* (2013.01)

(58) Field of Classification Search

CPC .... C07K 14/79; C12N 15/62; C12N 15/8257; A01K 67/0275

See application file for complete search history.

(56) References Cited

U.S. PATENT DOCUMENTS

| | | | |
|---|---|---|---|
| 5,723,125 | A | 3/1998 | Chang et al. |
| 6,111,081 | A | 8/2000 | Conneely et al. |
| 6,423,509 | B1 | 7/2002 | Sung et al. |
| 6,660,843 | B1 | 12/2003 | Feige et al. |
| 7,148,321 | B2 | 12/2006 | Gillies et al. |
| 7,229,962 | B2 | 6/2007 | Chung et al. |
| 8,273,351 | B2 | 9/2012 | TenHoor et al. |
| 9,809,641 | B2 | 11/2017 | Sato et al. |
| 2008/0004206 | A1 | 1/2008 | Rosen et al. |
| 2015/0093382 | A1 | 4/2015 | Sato et al. |
| 2018/0072794 | A1 | 3/2018 | Sato et al. |

FOREIGN PATENT DOCUMENTS

| | | | |
|---|---|---|---|
| EP | 1932855 | A1 | 6/2008 |
| JP | 2000511424 | A | 9/2000 |
| JP | 2002520045 | A | 7/2002 |

(Continued)

OTHER PUBLICATIONS

Jazayeri, et al., "Fc-Based Cytokines-Prospects for Engineering Superior Therapeutics", Biodrugs, 2008, 22, 11-26.

Yeung, et al., "Engineering Human IgG1 Affinity to Human Neonatal Fc Receptor: Impact of Affinity Improvement on Pharmacokinetics in Primates", J. Immunol., 2009, 182, 7663-7671.

Suzuki, et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR", J. Immunol., 2010, 184, 1968-1976.

(Continued)

*Primary Examiner* — Maryam Monshipouri

(74) *Attorney, Agent, or Firm* — Faegre Drinker Biddle & Reath LLP

(57) ABSTRACT

The present invention provides a lactoferrin fusion protein having high clinical utility and a production method therefor. The present invention further provides: a lactoferrin fusion protein that retains the biological activity of native lactoferrin while having a significantly extended in vivo life span, and that has more clinical utility than native lactoferrin and recombinant lactoferrin; and a production method therefor. With this fusion protein or a variant thereof, the ability of lactoferrin to bind iron is retained, and therefore at least the important biological activity of lactoferrin that is based on the iron-binding ability is retained. Additionally, this fusion protein or variant thereof has bioavailability and resistance to protease, and thus can exhibit biological activity in vivo over a long period. Furthermore, this fusion protein is not easily broken down by pepsin in the stomach.

17 Claims, 17 Drawing Sheets

Specification includes a Sequence Listing.

(56) References Cited

FOREIGN PATENT DOCUMENTS

| | | | |
|---|---|---|---|
| JP | 2003512011 | A | 4/2003 |
| JP | 2004521655 | A | 7/2004 |
| JP | 2007105044 | A | 4/2007 |
| JP | 2008509153 | A | 3/2008 |
| JP | 4234438 | B2 | 3/2009 |
| JP | 2010514699 | A | 5/2010 |
| JP | 2010-138160 | A | 6/2010 |
| JP | 2010-215522 | A | 9/2010 |
| JP | 2010531134 | A | 9/2010 |
| JP | 2011523351 | A | 8/2011 |
| JP | 2015-27981 | A | 2/2015 |
| JP | 5855239 | B2 | 2/2016 |
| JP | 2016-117717 | A | 6/2016 |
| WO | WO-2006017688 | A2 | 2/2006 |
| WO | WO-20080080042 | A2 | 7/2008 |
| WO | WO-2008147143 | A2 | 12/2008 |

OTHER PUBLICATIONS

Batra, et al., "Insertion of Constant Region Domains of Human IgG1 Into CD4-PE40 Increases Its Plasma Half-Life", Mol Immunol., 1993, 30, 379-386.

Dimitrov, D.S., "Review-Engineered CH2 domains (nanoantibodies)", mAbs, 2009, 1, 26-28.

Gong, et al., "Shortened Engineered Human Antibody CH2 Domains: Increased Stabilty and Binding to the Human Neonatal Receptor", J. Biol. Chem., 2011, 286, 27288-27293.

PCT/2013/062685—International Search Report dated Jul. 16, 2013.

Japanese Application No. 2014-512737—Office Action dated May 19, 2015 (with translation).

JP Application No. 2014-512737—Notice of Reasons for Rejection dated Aug. 25, 2015.

EP Application No. 13780579.2—Extended European Search Report dated Dec. 15, 2015.

Jan Terje Andersen, et al., "Extending Half-life by Indirect Targeting of the Neonatel Fc Receptor (FcRn) Using a Minimal Albumin Binding Domain", The Journal of Biological Chemistry, Feb. 18, 2011, vol. 286, No. 7, pp. 5234-5241.

Se Jin Im, et al., "Natural Form of Noncytolytic Flexible Human Fc as a Long-Acting Carrier of Agnostic Ligand, Erythropoietin", Sep. 2011, PLoS One 6(9), e24574.

Mikayama et al., (1993) Proc. Natl. Acad. Sci. US vol. 90, pp. 10056-10060.

Voet, et al., (1990) Biochemistry John Wiley & Sons, Inc., pp. 126-128 and 228-234.

Anderson et al., "Structure of human lactoferrin at 3.2-Å resolution," Proc. Natl. Acad. Sci., Apr. 1987, vol. 84, pp. 1769-1773.

Pierce, et al., "Molecular cloning and sequence analysis of bovine lactotransferrin," Eur. J. Biochem., 1991, vol. 196, pp. 177-184.

PCT/JP2017/038866—International Search Report dated Mar. 6, 2018.

Giansanti, et al., "Lactoferrin from Milk: Nutraceutical and Pharmacological Properties", Pharmaceuticals, Sep. 27, 2016; 9(4). pii: E61.

Suzuki, et al., "Molecular Cloning and Functional Expression of a Human Intestinal Lactoferrin Receptor", Biochemistry, Dec. 25, 2001; 40(51); pp. 15771-15779.

Ono, et al., "Effects of pepsin and trypsin on the anti-adipogenic action of lactoferrin against pre-adipocytes derived from rat mesenteric fat", British Journal of Nutrition, 2001, vol. 105, pp. 200-211.

Bern, et al., "The role of albumin receptors in regulation of albumin homeostasis: Implications for drug delivery", Journal of Controlled Release 211, 2015, pp. 144-162.

D. Sleep, et al., "Albumin as a versatile platform for drug half-life extension", Biochim. Biophys. Acta (2013), http://dx.doi.org/10.1016/j.bbagen.2013.04.023.

EP Application No. 17865762.3—Extended European Search Report dated Mar. 9, 2020.

Anderson, Bryan F., et al., "Apolactoferrin structure demonstrates ligand-induced conformational change in transferrins," Nature Apr. 19, 1990, vol. 344, pp. 784-787.

Shiga Y, Oshima Y, Kojima Y, et al., "Recombinant human lactoferrin-Fc fusion with an improved plasma half-life," Eur J Pharm Sci. 2015;67:136-143. doi:10.1016/j.ejps.2014.11.005.

Shiga Y, Murata D, Sugimoto a, et al., "Hinge-Deficient IgG1 Fc Fusion: Application to Human Lactoferrin," Mol Pharm. 2017;14(9):3025-3035. doi:10.1021/acs.molpharmaceut.7b00221.

Purification of HSA-HLF on a heparin carrier

Buffer: 10 nM HCl (pH 1.9)
Pepsin: final concentration 20 ng/ml
Each protein concentration: 0.5 mg/ml

LACTOFERRIN/ALBUMIN FUSION PROTEIN AND PRODUCTION METHOD THEREFOR

CROSS REFERENCE TO RELATED APPLICATIONS

This application is the National Stage of International Application No. PCT/JP2017/038866, filed Oct. 27, 2017, and claims benefit of Japanese Application No. 2016-212077 filed on Oct. 28, 2016 and Japanese Application No. 2017-044893 filed on Mar. 9, 2017.

REFERENCE TO A SEQUENCE LISTING

The instant application contains a sequence listing which has been submitted in ASCII format via EFS-Web and is hereby incorporated by reference in its entirety. Said ASCII copy, created on Aug. 14, 2018, is named G1649WO_Sequence_Listing.txt and is 77,437 bytes in size.

TECHNICAL FIELD

The present invention relates to a lactoferrin/albumin fusion protein and a production method thereof.

BACKGROUND ART

Lactoferrin is a glycoprotein having a molecular weight of about 80,000, which occurs mainly in mammalian milk and is also found in neutrophils, tears, saliva, nasal discharge, bile, semen, etc. Because of its iron-binding ability, lactoferrin belongs to the transferrin family. Known physiological activities of lactoferrin include an antibacterial effect, an iron metabolism regulatory effect, a cell proliferation activation effect, a hematopoietic effect, an anti-inflammatory effect, an antioxidative effect, a phagocytosis enhancement effect, an antiviral effect, a bifidobacteria growth promotion effect, an anticancer effect, a cancer metastasis inhibitory effect, a translocation inhibitory effect and so on. Further, recent studies have indicated that lactoferrin also has a lipid metabolism improvement effect, an analgesic or anti-stress effect, and an anti-aging effect (Non-patent Document 1, Non-patent Document 2).

As described above, lactoferrin is a multifunctional physiologically active protein having a wide range of functions and is therefore expected for use in, e.g., pharmaceutical and/or food applications for the purpose of restoration or promotion of health. Food products containing lactoferrin have already been commercially available. When administered orally, lactoferrin places fewer burdens on the administered subject than when injected. Moreover, lactoferrin receptors are known to be present on the small intestinal mucosa, and recent studies have indicated that a small amount of lactoferrin is taken up into the body through the intestinal tract to exert its biological activities (Non-patent Document 3). However, when given orally, lactoferrin will be hydrolyzed by the action of pepsin, an acidic protease contained in the gastric juice, and then cleaved into peptides. For this reason, most of the lactoferrin molecules given orally are unable to reach the intestinal tract (Non-patent Document 4). Thus, for enhancement of the lactoferrin's biological activities, it is important to ensure that lactoferrin is allowed to reach the intestinal tract without being hydrolyzed by the action of pepsin in the gastric juice. Techniques known for this purpose include pharmaceutical modifications for enteric purposes, as exemplified by coating with an enteric layer containing a component which will not dissolve at low pH but will dissolve around the neutral pH range (Patent Document 1). However, these pharmaceutical modifications have the drawback of requiring complicated steps.

Moreover, when lactoferrin per se is formulated into injections, lactoferrin will be degraded in blood and more rapidly accumulated in the liver; and hence such injections have been reported to have low stability in blood. For this reason, fusion proteins fused with the Fc region of IgG for improved stability in blood have been used as pharmaceutical preparations, and similar techniques have also been developed for lactoferrin (Patent Document 2).

Moreover, for improvement of stability in blood, not only fusion with the Fc region of IgG, but also serum albumin fusion proteins have been developed (Non-patent Document 5, Non-patent Document 6) and are now on the market. Serum albumin is a protein having a molecular weight of about 66,000, which constitutes about 60% of serum proteins and has the highest content among proteins in serum. Although the function of serum albumin in blood vessels is to control the osmotic pressure in blood vessels by water holding, serum albumin also binds to fatty acids, hormones and/or drugs to thereby transport them to tissues in need thereof. In addition, adults produce about 9 grams of serum albumin per day, about 40% of which is distributed in blood vessels and the remaining 60% is distributed in any tissues other than blood vessels.

Furthermore, since serum albumin has a tendency to accumulate in tumors, pharmaceutical preparations comprising serum albumin fused with a high molecular compound (e.g., paclitaxel) for enhanced anticancer activity are now also on the market. As described above, serum albumin fusion proteins are not only stable in blood, but also allow selective transport to tumor tissues.

PRIOR ART DOCUMENTS

Patent Documents

Patent Document 1: JP 2015-027981 A

Patent Document 2: Japanese Patent No. 5855239

Non-Patent Documents

Non-patent Document 1: Pharmaceuticals (Basel). 2016 Sep. 27; 9(4). pii: E61. Lactoferrin from Milk Non-patent Document 2: Nutraceutical and Pharmacological Properties. Giansanti F, Panella G, Leboffe L, Antonini G Non-patent Document 3: Suzuki Y A, Shin K, Lonnerdal B. Biochemistry. 2001 Dec. 25; 40(51):15771-9

Non-patent Document 4: Ono T, Morishita S, Fujisaki C, Ohdera M, Murakoshi M, Iida N, Kato H, Miyashita K, Iigo M, Yoshida T, Sugiyama K, Nishino H. Br J Nutr. 2011 January; 105(2):200-11

Non-patent Document 5: Malin Bern, Kine Marita Knudsen Sand, Jeannette Nilsen, Inger Sandlie, Jan Terje Andersen, Journal of Controlled Release 211 (2015) 144-162)

Non-patent Document 6: Sleep D, Cameron J, Evans L R. Biochim Biophys Acta. 2013 December; 1830(12):5526-34

SUMMARY OF THE INVENTION

Problem to be Solved by the Invention

The present invention aims to provide a highly clinically useful lactoferrin fusion protein and a production method thereof, etc. More specifically, the present invention aims to provide a lactoferrin fusion protein, which is configured to retain the biological activities of naturally occurring lactoferrin, to have a significantly prolonged in vivo life time, and to be more clinically useful than naturally occurring lactoferrin and gene recombinant lactoferrin, and a production method thereof, etc.

Means to Solve the Problem

Namely, the present invention provides the following fusion protein and method.

(1) A fusion protein formed between:

(i) human serum albumin (HSA) or a fragment or peptide of human serum albumin; and (ii) lactoferrin or a biologically active fragment or peptide of lactoferrin, wherein the fusion protein is represented by:

(LF-*s*-Y)*n* or (Y-*s*-LF)*n*

[wherein LF represents lactoferrin or a biologically active fragment or peptide of lactoferrin, Y represents human serum albumin or a protein or peptide comprising a fragment of human serum albumin, s represents any amino acid sequence of 0 to 10 residues, and n represents an integer of 1 to 10], or a variant thereof.

(2) The fusion protein or variant thereof according to (1) above, wherein the fusion protein is represented by:

(LF-*s*-Y)*n*.

(3) The fusion protein or variant thereof according to (1) above, wherein the fusion protein is represented by:

(Y-*s*-LF)*n*.

(4) The fusion protein or variant thereof according to (1) above, which comprises the amino acid sequence shown in SEQ ID NO: 7.

(5) The fusion protein or variant thereof according to (1) above, which comprises the amino acid sequence shown in SEQ ID NO: 14.

(6) The fusion protein or variant thereof according to any one of (1) to (5) above, wherein the fusion protein or variant thereof retains 50% or more of the iron-chelating ability of naturally occurring or gene recombinant lactoferrin.

(7) The fusion protein or variant thereof according to any one of (1) to (6) above, wherein the fusion protein or variant thereof is taken up via at least one receptor selected from the group consisting of the lactoferrin receptor and the albumin receptor.

(8) The fusion protein or variant thereof according to any one of (1) to (7) above, wherein the fusion protein or variant thereof has improved pepsin resistance when compared to naturally occurring or gene recombinant lactoferrin.

(9) A nucleic acid molecule encoding the fusion protein or variant thereof according to any one of (1) to (8) above.

(10) An expression vector comprising the nucleic acid molecule according to (9) above.

(11) A host cell comprising the expression vector according to (10) above.

(12) A genetically modified non-human animal comprising the nucleic acid molecule according to (9) above.

(13) A therapeutic agent for diseases ameliorated by the fusion protein or variant thereof according to any one of (1) to (8) above.

(14) A pharmaceutical composition comprising the fusion protein or variant thereof according to any one of (1) to (8) above and a carrier.

(15) The pharmaceutical composition according to (15) above for use in tumor treatment.

(16) The pharmaceutical composition according to (16) above, wherein the tumor is lung cancer.

(17) A method for producing the fusion protein or variant thereof according to any one of (1) to (8) above, which comprises culturing a host cell comprising a gene encoding the fusion protein or variant thereof to express the fusion protein, and collecting the fusion protein or variant thereof from the host cell or the medium thereof.

(18) A method for tumor treatment, which comprises administering a patient with a therapeutically effective amount of the fusion protein or variant thereof according to (1) above.

(19) The method according to (18) above, wherein the tumor is lung cancer.

(20) The fusion protein or variant thereof according to (1) above for use in tumor treatment.

(21) The fusion protein or variant thereof according to (20) above, wherein the tumor is lung cancer.

(22) Use of the fusion protein or variant thereof according to (1) above in the manufacture of a pharmaceutical composition for use in tumor treatment.

(23) The use according to (22) above, wherein the tumor is lung cancer.

The fusion protein of the present invention or a variant thereof (hereinafter may also be referred to as "the fusion protein or the like") retains the iron-binding ability of lactoferrin and at least retains the important biological activities of lactoferrin, which are based on the iron-binding ability. Moreover, because of having bioavailability and resistance against proteases, the fusion protein or the like can exert its biological activities in vivo over a long period of time. Further, the fusion protein of the present invention is characterized by being more resistant to digestion and cleavage with pepsin in the stomach. Due to this property, the fusion protein of the present invention is able to fully reach the intestine without requiring any additional pharmaceutical modifications for enteric purposes, as exemplified by coating with an enteric layer containing a component which will not dissolve at low pH but will dissolve around the neutral pH range.

Lactoferrin is extremely safe and has a wide range of biological activities. Thus, the present invention allows more advantageous application of lactoferrin as a therapeutic or prophylactic agent for diseases or symptoms for which no effective therapeutic agent has been available. For example, the fusion protein of the present invention can be applied to a wider range of diseases or symptoms, such as lifestyle-related diseases (e.g., arteriosclerosis, hypercholesterolemia, hyperlipidemia, hypertension, diabetes, fatty liver), cancers (e.g., prevention of carcinogenesis, secondary prevention of cancers, suppression of metastasis, enhanced effects of carcinostatic agents), autoimmune diseases (e.g., dry eye and dry mouth associated with Sjogren's syndrome, rheumatic arthritis, malignant rheumatoid arthritis, collagenosis, multiple sclerosis, systemic lupus erythematosus, systemic lupus erythematosus), psychoneurotic diseases (e.g., dementia, Alzheimer's disease, Parkinson's disease, epilepsy, depression, social withdrawal, schizophrenia, various stress-induced diseases, climacteric symptoms), hepatitis (e.g., various types of virus hepatitis, nonalcoholic hepatitis, cirrhosis), inflammatory bowel diseases (e.g., ulcerative colitis, Crohn's disease), irritable bowel syndrome, benign prostatic hyperplasia, frequent urination, insomnia, constipation and so on. Further, since lactoferrin has an antibacterial or antiviral effect and an immunostimulatory effect, the fusion protein of the present invention or a pharmaceutical composition comprising the same can also be applied to various types of infections and their associated inflammation, as exemplified by gastric mucosal infection with *Helicobacter pylori*, periodontal disease, pyorrhea alveolaris, ozostomia, oral candidiasis, stomatitis, angular cheilitis, rhinitis, esophagitis, cholecystitis, urinary tract infections, vaginal infections, tinea pedis, acne, infections with viruses of the herpes group, senile pneumonia, post-operative infections and so on, and it also has the effect of enhancing the action of antibiotics. On the other hand, lactoferrin also acts to provide immunological tolerance, and hence the fusion protein of the present invention or a pharmaceutical composition comprising the same can also be applied to allergic diseases such as pollinosis, atopic dermatitis, seborrhea, urticaria and so on. Notably, lactoferrin has a strong anti-oxidative stress effect based on its iron-chelating effect, and hence the fusion protein of the present invention or a pharmaceutical composition comprising the same can also be applied not only to Wilson's disease, fulminant hepatitis and so on, but also to anti-aging and rejuvenation effects on the skin and eyes, age-related macular degeneration, diabetic retinopathy, anti-keratinization and rejuvenation effects on mucosal epithelial cells, etc.

DESCRIPTION OF EMBODIMENTS

Figure 1:
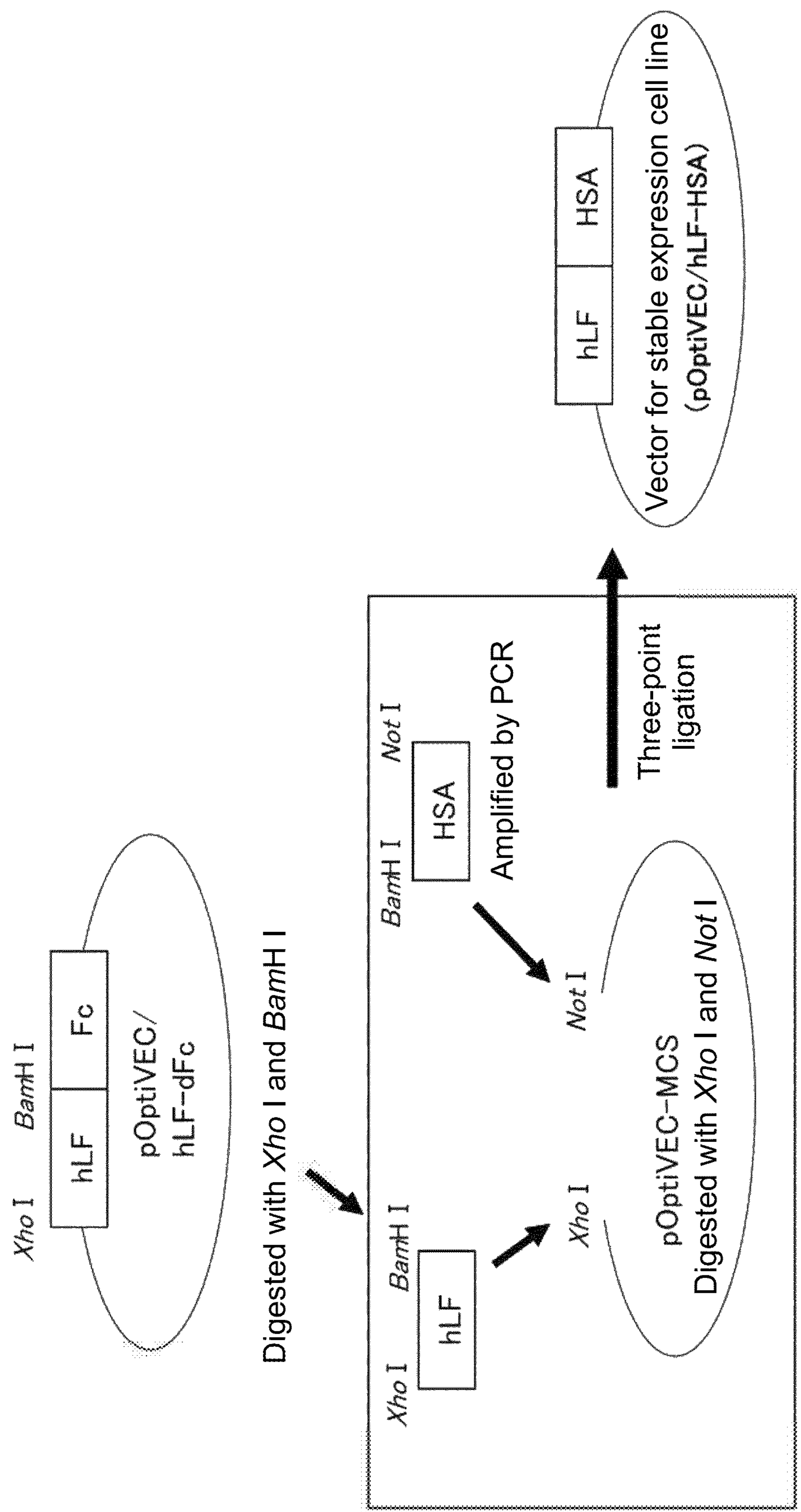
FIG. 1 shows a schematic representation where human lactoferrin (hLF) cDNA comprising a signal sequence is fused with human serum albumin (HSA) cDNA prepared by PCR techniques to thereby prepare a hLF-HSA fusion protein expression vector (pOptiVEC/hLF-HSA).

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2016-212077 (filed on Oct. 28, 2016) and Japanese Patent Application No. 2017-044893 (filed on Mar. 9, 2017), based on which the present application claims priority.

The present invention will be described in more detail below. The following embodiments are illustrated to describe the present invention, and it is not intended to limit the present invention only to these embodiments. The present invention can be implemented in various modes, without departing from the spirit of the present invention. It should be noted that all publications cited herein, including prior art documents, patent gazettes and other patent documents, are incorporated herein by reference. It should be noted that amino acid sequences are represented herein in the N-terminal to C-terminal direction, while nucleotide sequences are represented herein in the 5'-terminal to 3'-terminal direction, unless otherwise specified.

Moreover, as used herein, the term "about" is intended to mean a range of ±10%, ±5%, ±3%, ±2% or ±1% of each numerical value following this term.

The fusion protein of the present invention with lactoferrin or a biologically active fragment or peptide of lactoferrin is represented by the following general formula.

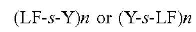

$$(LF\text{-}s\text{-}Y)n \text{ or } (Y\text{-}s\text{-}LF)n \qquad \text{formula I}$$

In formula I, LF represents lactoferrin or a biologically active fragment or peptide of lactoferrin, Y represents human serum albumin or a protein or peptide comprising a fragment of human serum albumin, and s represents any amino acid sequence of 0 to 10 residues, where n represents an integer of 1 to 10. Moreover, (LF-s-Y) represents a protein fused such that hLF is located at the N-terminal side and HSA is located at the C-terminal side, while (Y-s-LF) represents a protein fused such that HSA is located at the N-terminal side and hLF is located at the C-terminal side.

The fusion protein of (LF-s-Y)n may be exemplified by proteins comprising or consisting of the amino acid sequence shown in SEQ ID NO: 7 or an amino acid sequence sharing a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence of SEQ ID NO: 7. In a certain embodiment, the fusion protein of (LF-s-Y)n is a protein consisting of the amino acid sequence shown in SEQ ID NO: 7.

The fusion protein of (Y-s-LF)n may be exemplified by proteins comprising or consisting of the amino acid sequence shown in SEQ ID NO: 14 or an amino acid sequence sharing a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence of SEQ ID NO: 14. In a certain embodiment, the fusion protein of (Y-s-LF)n is a protein consisting of the amino acid sequence shown in SEQ ID NO: 14.

The fusion protein of the present invention is a biologically active fusion protein comprising human serum albumin (HSA) or a fragment of human serum albumin and lactoferrin or a biologically active fragment or peptide of lactoferrin.

Human Serum Albumin (HSA)

In the fusion protein of the present invention, it is possible to use the whole molecule of albumin or a partial peptide of albumin, which may be biocompatible or pharmacologically inert. Albumin available for use may be derived from humans or any other various animals (e.g., cow, horse, pig, sheep, goat, camel) or derived from hen eggs, but preferred is human serum albumin (HSA). The amino acid sequence (GenBank: AAA98797.1; SEQ ID NO: 2) and CDS sequence (GenBank: M12523.1; SEQ ID NO: 1) of human serum albumin are known.

For use in the present invention, human serum albumin may be of the same sequence as the naturally occurring sequence (SEQ ID NO: 2) or may comprise a mutation(s). Moreover, human serum albumin comprising a mutation(s) may be exemplified by proteins having an amino acid sequence sharing a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence of SEQ ID NO: 2. In general, a larger numerical value is more preferred for the above sequence identity. As a fragment or peptide of human serum albumin, it is possible to use a fragment or peptide consisting of a sequence which accounts for 10% or more, 20% or more, 30% or more, 40% or more, 50% or more, 60% or more, 70% or more, 80% or more, or 90% or more of the amino acid sequence of SEQ ID NO: 2.

Lactoferrin

Lactoferrin for use in the present invention may have the same amino acid sequence as naturally occurring lactoferrin obtained from humans or any other various animals (e.g., cow, horse, pig, sheep, goat, camel) or may comprise partial deletion, addition or substitution of amino acids as long as it has the desired physiological activities of lactoferrin. The amino acid sequence (GenBank: AAN75578.2; SEQ ID NO: 4) and CDS sequence (GenBank: AY178998.2; SEQ ID NO: 3) of human lactoferrin are known. Various candidates are known for such a functional (biologically active) fragment or peptide of lactoferrin (see, e.g., "Programs and Abstracts of the 2nd Clinical Lactoferrin Symposium 2009," pages 21 to 27 (Keiichi Shimazaki), which may be designed as needed on the basis of the descriptions in the above document, etc. In the case of using lactoferrin comprising a mutation(s), examples include proteins having an amino acid sequence sharing a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence of SEQ ID NO: 4. In general, a larger numerical value is more preferred for the above sequence identity.

In relation to the fusion protein or the like of the present invention, the physiological activities of lactoferrin are intended to mean a wide range of physiological activities including an antibacterial effect, an iron metabolism regulatory effect, a cell proliferation activation effect, a hematopoietic effect, an anti-inflammatory effect, an antioxidative effect, a phagocytosis enhancement effect, an antiviral effect, a bifidobacteria growth promotion effect, an anticancer effect, a cancer metastasis inhibitory effect, a translocation inhibitory effect, a lipid metabolism improvement effect, an analgesic effect, an anti-stress effect and so on. These effects allow treatment (including amelioration) and prevention of many diseases or symptoms including lifestyle-related diseases (e.g., hypercholesterolemia, hyperlipidemia), pain control (e.g., cancer pain, neuropathic pain), collagenosis (e.g., dry eye and dry mouth associated with Sjogren's syndrome, rheumatic arthritis), periodontal disease, hepatitis C, etc. As a biologically active fragment or peptide of lactoferrin, it is possible to use a fragment or peptide consisting of a sequence which accounts for 10% or more, 20% or more, 30% or more, 40% or more, 50% or more, 60% or more, 70% or more, 80% or more, or 90% or more of the amino acid sequence of SEQ ID NO: 4. More preferably, as a biologically active fragment or peptide of lactoferrin, it is possible to use a fragment or peptide consisting of a contiguous amino acid sequence which accounts for 10% or more, 20% or more, 30% or more, 40% or more, 50% or more, 60% or more, 70% or more, 80% or more, or 90% or more of the amino acid sequence of SEQ ID NO: 4.

In particular, the fusion protein of the present invention has the same iron-chelating (binding) ability as naturally occurring lactoferrin (or recombinant lactoferrin having a sequence equivalent to that of naturally occurring lactoferrin). More specifically, assuming that the iron-binding ability of naturally occurring lactoferrin (or recombinant lactoferrin having a sequence equivalent to that of naturally occurring lactoferrin) is set to 100%, as measured in the manner described later in the Example section, the fusion protein or the like of the present invention retains at least 50% or more (e.g., about 50% to about 150% or about 50% to about 120%) of the iron-binding ability. In a preferred embodiment, the fusion protein or the like of the present invention has iron-binding ability which corresponds to about 70% to about 100% or more (e.g., about 70% to about 150% or about 70% to about 120%), more particularly about 90% or more of that of naturally occurring lactoferrin (or recombinant lactoferrin having a sequence equivalent to that of naturally occurring lactoferrin). It should be noted that when the iron-binding ability is measured in the manner described in the Example section or in a manner equivalent thereto, there may be an error around ±2%, ±5%, ±10% or ±20%.

Human serum albumin for use in the present invention should be resistant to cleavage from the state fused with human lactoferrin. Moreover, the fusion protein of the present invention may be either hLF-HSA (i.e., a protein fused such that human lactoferrin is located at the N-terminal side and human serum albumin is located at the C-terminal side) or HSA-hLF (i.e., a protein fused such that human serum albumin is located at the N-terminal side and human lactoferrin is located at the C-terminal side). At least, hLF-HSA has properties excellent in thermal stability and pepsin digestion resistance.

Spacer Sequence

The fusion protein of the present invention may further comprise an additional amino acid sequence. The fusion protein of the present invention may have any amino acid sequence whose length is suitable for use as a spacer sequence between human serum albumin and lactoferrin or a biologically active fragment or peptide of lactoferrin. Such a spacer sequence (s) may be, for example, any amino acid sequence of 0 to 10 residues or 0 to 5 residues. Other additional sequences may be those providing three-dimensional structural advantages, as in the case of a spacer sequence, or may be those imparting some kind of function to the fusion protein, as exemplified by signal peptides or tag sequences used for purification purposes.

The fusion protein of the present invention is deemed to be taken up in the small intestine through at least one known receptor selected from the group consisting of the lactoferrin receptor and the albumin receptor (Malin Bern, Kine Marita Knudsen Sand, Jeannette Nilsen, Inger Sandlie, Jan Terje Andersen, Journal of Controlled Release 211 (2015) 144-162).

The fusion protein or the like of the present invention can be prepared by gene recombination technology. A lactoferrin gene having a desired amino acid sequence and a gene for human serum lactoferrin may be linked in a standard manner to construct an expression vector comprising other elements required for expression in desired host cells, and this vector may then be introduced into the host cells to express a fusion protein, followed by collecting the expressed fusion protein from the cells or medium (documented in Shiga, Y et al., Eur J Pharm Sci. Vol. 67, 136-143, 2015).

A nucleic acid molecule encoding the fusion protein or the like of the present invention can be designed and prepared by using known sequences and standard genetic engineering techniques (documented in Ikuta, S et al., J Control Release vol. 147, 17-23, 2010). Genes encoding lactoferrin and human serum albumin can be obtained by being cloned from commonly available various genomic or cDNA libraries with the use of probes based on known nucleic acid or amino acid sequences or by being synthesized by polymerase chain reaction (PCR). It is also possible to make desired modifications to these genes or introduce mutations into these genes.

A host cell-vector system used for replication of the nucleic acid molecule and a host-vector system used for expression of the fusion protein may be selected as appropriate from among many known systems of eukaryotic cells (e.g., mammalian cells, plant cells, yeast, insect cells) and prokaryotic cells (e.g., bacteria). In addition to a sequence encoding lactoferrin or a biologically active fragment or peptide of lactoferrin and a sequence encoding human serum albumin (or alternatively, a sequence encoding human serum albumin and a sequence encoding lactoferrin or a biologically active fragment or peptide of lactoferrin), the vector used to express the fusion protein of the present invention generally comprises, in an operably linked state, a transcription promoter, a secretory signal peptide sequence, a transcription terminator, a polyA signal and other elements, and usually further comprises a selective marker such as a drug resistance gene.

These vectors may be used to transform host cells in accordance with various known techniques.

The fusion protein of the present invention can be produced by genetically modified plants and genetically modified animals prepared for this purpose. For example, a nucleic acid molecule encoding the fusion protein of the present invention may be integrated into the non-human animal (e.g., sheep, goat) genome to thereby allow the fusion protein of the present invention to be secreted into milk. Alternatively, upon integration into plants, it is possible to prepare useful plants which produce the fusion protein or the like of the present invention (see, e.g., JP 2004-528022 A).

The fusion protein of the present invention can be isolated and purified from the medium of host cells transformed with the expression vector of the present invention by using ammonium sulfate precipitation, gel filtration, and various chromatographic techniques such as ion exchange chromatography and affinity chromatography, as appropriate. A particularly preferred purification technique is ion exchange chromatography.

The fusion protein of the present invention fully retains the biological activities of lactoferrin, and hence can be administered as a prophylactic or therapeutic agent for diseases against which lactoferrin is effective, either alone or in combination with other pharmaceutical agents. Moreover, the fusion protein of the present invention can be formulated into pharmaceutical compositions in desired dosage forms by being blended with various carriers, therapeutically inert bases and/or additives known in the pharmaceutical field. For convenience' sake, the term "pharmaceutical preparation" or "pharmaceutical composition" used in relation to the present invention is intended to include not only cases where subjects to be administered are humans, but also cases where subjects to be administered are animals (i.e., veterinary drugs and the like). Various ingredients, which can be contained in such a pharmaceutical composition, and possible dosage forms are well known to those skilled in the art.

Pepsin Resistance

The fusion protein of the present invention has improved pepsin resistance. Since pepsin is a major protease in the gastric juice, a fusion protein which is more resistant to digestion in the stomach can be provided when its resistance to pepsin is improved. Pepsin resistance can be measured by known procedures. For example, to a protein solution whose concentration has been adjusted as appropriate, a pepsin solution is added to cause digestion, followed by gel electrophoresis such as SDS-PAGE to detect or quantify the digested proteins, whereby pepsin resistance can be measured (Yasuhiro Nojima, Yosuke Suzuki, Kazuhiro Yoshida, Fumiko Abe, Tuneo Shiga, Takashi Takeuchi, Akihiko Sugiyama, Hirohiko Shimizu, and Atsushi Sato, Pharmaceutical Research, Vol. 26, No. 9, September 2009 2125-2132). For example, if no significant proteolysis product is observed by gel electrophoresis after the above pepsin treatment, such a case can be determined to have pepsin resistance. Moreover, if proteolysis products generated by pepsin treatment are reduced in a fusion protein when compared to naturally occurring or gene recombinant lactoferrin, such a fusion protein can be determined to have improved pepsin resistance.

Antitumor Activity

The fusion protein of the present invention has antitumor activity. The antitumor activity intended here refers to the activity to inhibit the proliferation of tumor cells. The antitumor activity is also herein referred to as an antitumor effect.

The antitumor activity of the fusion protein of the present invention can be confirmed as follows: in the presence (sample group) and in the absence (control group) of the fusion protein of the present invention, culture is started from the same number of tumor cells and, after a certain period of time has passed (e.g., after 24 hours, after 48 hours, after 72 hours), the number of tumor cells in the sample group is confirmed to be smaller than the number of tumor cells in the control group.

The tumor intended here may be either a benign tumor or a malignant tumor. Examples of such a tumor include (1) sarcomas such as osteosarcoma and soft tissue sarcoma, etc., (2) cancers such as breast cancer, lung cancer, bladder cancer, thyroid cancer, prostate cancer, colon cancer, colorectal cancer, pancreatic cancer, gastric cancer, liver cancer, uterine cancer, uterine cervical cancer, ovarian cancer, etc., (3) lymphomas such as Hodgkin's and non-Hodgkin's lymphomas, etc., (4) neuroblastoma, (5) melanoma, (6) myeloma, (7) Wilms tumor, (8) leukemia such as acute myelogenous leukemia (AML), chronic myelogenous leukemia (CML), acute lymphocytic leukemia (ALL) and chronic lymphocytic leukemia (CLL), etc., (9) glioma, (10) retinoblastoma and so on, but are not limited thereto. In a certain embodiment, the tumor is lung cancer, more particularly lung adenocarcinoma. Moreover, tumor cells may be of any type, i.e., differentiated type, poorly differentiated type or undifferentiated type. However, in a certain embodiment, the fusion protein of the present invention exerts a particularly strong antitumor effect against tumor cells of differentiated type and poorly differentiated type.

Interestingly, the fusion protein of the present invention has remarkably higher antitumor activity than HSA or rhLF when administered alone. Moreover, the fusion protein of the present invention (i.e., HSA and rhLF covalently linked to each other) shows higher antitumor activity than HSA and rhLF when used in combination without being covalently linked to each other. Further, the fusion protein of the present invention exerts a cell proliferation effect selectively on tumor cells, and exerts no cell proliferation effect on normal cells. For this reason, the fusion protein of the present invention is shown to exert antitumor activity with no or little side effects if any.

The present invention further provides a method for tumor treatment, which comprises administering a patient with a therapeutically effective amount of the fusion protein of the present invention or a variant thereof. In addition, the present invention provides the fusion protein of the present invention or a variant thereof for use in tumor treatment. Moreover, the present invention provides the use of the fusion protein of the present invention or a variant thereof in the manufacture of a pharmaceutical composition for use in tumor treatment. As used herein, the terms "therapeutically effective amount," "patient" and "administration"

Pharmaceutical Composition

The present invention provides a pharmaceutical composition comprising the fusion protein of the present invention for use in the treatment of lactoferrin-related diseases.

The lactoferrin-related diseases intended here include lifestyle-related diseases (e.g., arteriosclerosis, hypercholesterolemia, hyperlipidemia, hypertension, diabetes, fatty liver), cancers (e.g., prevention of carcinogenesis, secondary prevention of cancers, suppression of metastasis, enhanced effects of carcinostatic agents), autoimmune diseases (e.g., dry eye and dry mouth associated with Sjogren's syndrome, rheumatic arthritis, malignant rheumatoid arthritis, collagenosis, multiple sclerosis, systemic lupus erythematosus, systemic lupus erythematosus), psychoneurotic diseases (e.g., dementia, Alzheimer's disease, Parkinson's disease, epilepsy, depression, social withdrawal, schizophrenia, various stress-induced diseases, climacteric symptoms), pain relief (e.g., enhancement of opioids such as morphine, cancer pain, neuropathic pain, post-herpetic pain, fibromyalgia, postoperative pain, glossodynia, menstrual pain, toothache, arthralgia, climacteric symptoms), hepatitis (e.g., various types of virus hepatitis, nonalcoholic hepatitis, cirrhosis), inflammatory bowel diseases (e.g., ulcerative colitis, Crohn's disease), irritable bowel syndrome, benign prostatic hyperplasia, frequent urination, insomnia, constipation and so on. Further examples include diseases which may be treated based on the antiviral effect and immunostimulatory effect of lactoferrin, as exemplified by gastric mucosal infection with *Helicobacter pylori*, periodontal disease, pyorrhea alveolaris, ozostomia, oral candidiasis, stomatitis, angular cheilitis, rhinitis, esophagitis, cholecystitis, urinary tract infections, vaginal infections, tinea pedis, acne, infections with viruses of the herpes group, senile pneumonia, postoperative infections and so on, and further include allergic diseases which can be treated based on the immunological tolerance effect of lactoferrin, as exemplified by pollinosis, atopic dermatitis, seborrhea, urticaria and so on. Other examples of lactoferrin-related diseases include diseases which can be treated based on the anti-oxidative stress effect of lactoferrin, as exemplified by Wilson's disease, fulminant hepatitis and so on, as well as anti-aging and rejuvenation effects on the skin and eyes, age-related macular degeneration and diabetic retinopathy.

In addition, the present invention provides a pharmaceutical composition comprising the fusion protein of the present invention for use in tumor treatment. The tumor intended here is as discussed above.

Patients are not limited in any way as long as they are mammals, but preferred are humans. The patients intended here include fetuses.

The term "administration" is intended to mean that the fusion protein of the present invention is delivered into the body of a patient. The route of administration is not limited in any way, and may be either the oral route or the parenteral route. In the case of administration via the parenteral route, it may be intravenous administration, intraperitoneal administration, intramuscular injection, percutaneous administration, nasal administration, sublingual administration, or topical administration.

The composition of the present invention may comprise the fusion protein of the present invention serving as an active ingredient in a therapeutically effective amount. As used herein, the term "therapeutically effective amount" refers to an amount which results in alleviation or no exacerbation of symptoms in a disease to be treated when an active ingredient is administered in this amount to a subject in comparison with when the same active ingredient is not administered. This term also encompasses the meaning of a prophylactically effective amount.

For example, in the case of oral administration, the therapeutically effective amount may be set to 0.001 to 10 g/kg/day, 0.005 to 10 g/kg/day, 0.01 to 10 g/kg/day, or 0.01 to 5 g/kg/day as the dose of lactoferrin or a biologically active fragment or peptide of lactoferrin. For use in humans, the therapeutically effective amount is generally 10 mg to 15,000 mg, 10 mg to 12,000 mg, 10 mg to 10,000 mg, 20 mg to 10,000 mg, 20 mg to 8,000 mg, 30 mg to 8,000 mg, or 30 mg to 6,000 mg as the daily dose of lactoferrin or a biologically active fragment or peptide of lactoferrin. Likewise, in the case of percutaneous administration, the therapeutically effective amount may be set to 0.001 to 10 g/kg/day, 0.005 to 10 g/kg/day, 0.01 to 10 g/kg/day, or 0.01 to 5 g/kg/day as the dose of lactoferrin or a biologically active fragment or peptide of lactoferrin. For use in humans, the therapeutically effective amount is generally 10 mg to 15,000 mg, 10 mg to 12,000 mg, 10 mg to 10,000 mg, 20 mg to 10,000 mg, 20 mg to 8,000 mg, 30 mg to 8,000 mg, or 30 mg to 6,000 mg as the daily dose of lactoferrin or a biologically active fragment or peptide of lactoferrin. Such a daily dose may be administered as a single dose or in divided doses to a patient in need of treatment.

It should be noted that the dosage and administration frequency of the composition of the present invention will vary depending on various factors, such as the species, body weight, sex and age of a subject, the progression of disease, the route of administration, etc., but those skilled in the art including physicians, veterinarians, dentists or pharmacists would be able to determine the dosage in consideration of these respective factors.

The numerical values listed above are merely typical ones to describe the therapeutically effective amount, dosage and administration frequency; and hence it is highly probable that a therapeutic effect will be provided even at a numerical value higher or lower than those listed above. Thus, even numerical values higher or lower than those listed above for the therapeutically effective amount, dosage and administration frequency also fall within the therapeutically effective amount, dosage and administration frequency intended in the pharmaceutical composition of the present invention.

The effective dose of a therapeutic agent or pharmaceutical composition comprising the fusion protein or the like of the present invention will vary depending on the type or severity of disease or symptom to be treated or prevented, the state of a subject to be administered, the intended dosage form, the route of administration and so on, and hence may be selected as appropriate based on the known effective doses of lactoferrin and albumin.

EXAMPLES

Example 1: Preparation of Fusion Proteins Between Human Lactoferrin (hLF) and Human Serum Albumin (HSA)

As to fusion proteins formed between human lactoferrin (hLF) and human serum albumin (HSA), a protein fused such that hLF is located at the N-terminal side and HSA is located at the C-terminal side is designated as hLF-HSA, whereas a protein fused such that HSA is located at the N-terminal side and hLF is located at the C-terminal side is designated as HSA-hLF. Moreover, as used herein, rhLF refers to *Aspergillus*-derived recombinant hLF.

1. Construction of a hLF-HSA Expression Vector

A hLF cDNA fragment comprising a signal sequence was prepared from the known expression vector pOptiVEC/hLF-dFc (Shiga, Y et al., Eur J Pharm Sci. Vol. 67, 136-143, 2015) for DHFR-deficient Chinese hamster ovary cells (CHO [DG44]) by digestion with Xho I and BamH I.

On the other hand, human HSA cDNA was obtained as follows using the vector pPIC9-HSA-trx (Ikuta, S et al., J Control Release vol. 147, 17-23, 2010) as a template. Using BamHI-c-HSA(73-92) (5'-CGCGGATCCC-GATGCACACAAGAGTGAGGT-3': SEQ ID NO: 5) [designed to introduce a BamH I site (underlined) at the upstream side]) as a forward primer and using NotI-HSA (1830-1811) (5'-AAGGAAAAAAGCGGCCGCT-TATAAGCCTAAGGCAGCTT-3': SEQ ID NO: 6) [designed to introduce a Not I site (underlined) at the 3'-terminal side] as a reverse primer, PCR was conducted with the DNA synthetase "PrimeStar® HS (premix)" (trade name, Takara Bio Inc., Japan) to obtain HSA cDNA. The resulting DNA fragment was digested with BamH I and Not I to excise a DNA fragment of human HSA.

The previously reported expression vector pOptiVEC-MCS (Shiga, Y et al., Eur J Pharm Sci. Vol. 67, 136-143, 2015) for DHFR-deficient Chinese hamster ovary cells (CHO [DG44]) was digested with Xho I and Not I, followed by three-point ligation with the above Xho I/BamH I-digested human hLF cDNA fragment and the above BamH I/Not I-digested human HSA cDNA fragment using T4 DNA ligase (Nippon Gene Co., Ltd., Japan) to prepare pOptiVEC/hLF-HSA, a vector for stable expression CHO (DG44) cell lines (FIG. 1). The nucleotide sequence of the resulting hLF-HSA fusion region was confirmed by dideoxy sequencing. The amino acid sequence of a human serum albumin (HSA)/human lactoferrin (hLF) fusion protein encoded by the fusion protein HSA-hLF expression vector pOptiVEC/hLF-HSA is shown as a hLF-HSA sequence (SEQ ID NO: 7). In this hLF-HSA sequence, amino acid positions 1 to 711 (SEQ ID NO: 8) correspond to the amino acid sequence of human lactoferrin (hLF) comprising a signal sequence, amino acid positions 712 to 713 (the sequence Asp-Pro) correspond to the amino acid sequence of a spacer, and amino acid positions 714 to 1298 (SEQ ID NO: 9) correspond to the amino acid sequence of human serum albumin (HSA).

2. Construction of a HSA-hLF Expression Vector

HSA cDNA comprising a signal sequence was obtained as follows. Total RNA was extracted from the human liver cancer cell line HepG2 and this Total RNA was used as a template for RT-PCR. HepG2 was cultured in 10% fetal bovine serum (FBS)-supplemented D-MEM (low glucose) medium (Wako Pure Chemical Industries, Ltd., Japan). From $1\times10^6$ cells of HepG2 cells, Total RNA was extracted using an RNA extraction reagent, ISOGEN (trade name, Nippon Gene Co., Ltd., Japan), in accordance with the protocols attached to the reagent. The resulting 2 μg Total RNA was used as a template to synthesize Total cDNA with oligo dT primers (oligo $(dT)_{15}$, Promega) and reverse transcriptase (ReverTra Ace, trade name, Toyobo Co., Ltd., Japan) in accordance with the protocols attached to the reagents. A HSA cDNA fragment was obtained by PCR using the resulting Total cDNA as a template. Using N-EcoRI-HSA (5'-CGGAATTCAT-GAAGTGGGTAACCTTTAT-3': SEQ ID NO: 10) [designed to introduce an EcoR I site (underlined) upstream of the initiation codon ATG] as a forward primer and using HSA-XhoI-C (5'-CCGCTCGAGTAAGCCTAAGGCAGCTTGAC-3': SEQ ID NO: 11) [designed to introduce an Xho I site (underlined)

at the 3'-terminal side] as a reverse primer, HSA cDNA was amplified with the DNA synthetase "PrimeStar® HS (premix)" (trade name, Takara Bio Inc., Japan). The resulting DNA fragment was subjected to addition of A with rTaq DNA polymerase (trade name, Toyobo Co., Ltd., Japan) and TA cloning with "pGEMT® Easy vector" (trade name, Promega). The nucleotide sequence of HSA cDNA was confirmed by dideoxy sequencing. Then, this vector was digested with EcoR I and Xho I to excise a DNA fragment of human HSA comprising a signal sequence.

On the other hand, a hLF cDNA fragment was obtained as follows using the known vector "pBSIILfAL" comprising the full-length hLF cDNA sequence (Shiga, Y et al., Eur J Pharm Sci. Vol. 67, 136-143, 2015) as a template. Using S_LFex_XhoI_ATG (5'-CTCGAGATGGGCCGTAGGA-3': SEQ ID NO: 12) [designed to introduce an Xho I site (underlined) at the upstream side]) as a forward primer and using hLF reverse (Not-hLF-2136R) (5'-GCGGCCGCTTACTTCCTGAGGAACTCAC-3': SEQ ID NO: 13) [designed to introduce a Not I site (underlined) at the 3'-terminal side] as a reverse primer, hLF cDNA was amplified with the DNA synthetase "PrimeStar HS (premix)" (trade name, Takara Bio Inc., Japan). The resulting DNA fragment was subjected to addition of A with rTaq DNA polymerase (trade name, Toyobo Co., Ltd., Japan) and TA cloning with "pGEM®-T Easy vector" (trade name, Promega). The nucleotide sequence of hLF cDNA was confirmed by dideoxy sequencing. Then, this vector was digested with Xho I and Not I to excise a human hLF cDNA fragment.

Figure 2:
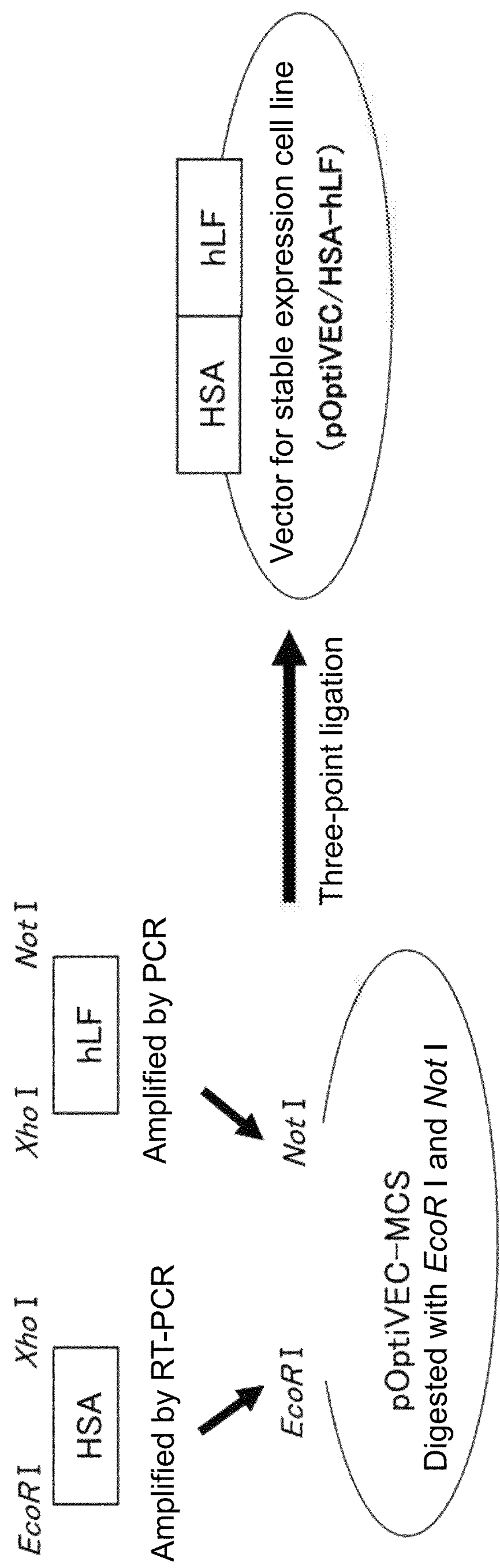
FIG. 2 shows a schematic representation where human serum albumin (HSA) cDNA comprising a signal sequence is fused with human lactoferrin (hLF) cDNA prepared by PCR techniques to thereby prepare a HSA-hLF fusion protein expression vector (pOptiVEC/HSA-hLF).

The previously reported expression vector pOptiVEC-MCS (Shiga, Y et al., Eur J Pharm Sci. Vol. 67, 136-143, 2015) for DHFR-deficient Chinese hamster ovary cells (CHO [DG44]) was digested with EcoR I and Not I, followed by three-point ligation with the above EcoR I/Xho I-digested human HSA cDNA fragment and the above Xho I/Not I-digested human hLF cDNA fragment using T4 DNA ligase (Nippon Gene Co., Ltd., Japan) to prepare pOptiVEC/HSA-hLF, a vector for stable expression CHO (DG44) cell lines (FIG. 2).

The amino acid sequence of a human serum albumin (HSA)/human lactoferrin (hLF) fusion protein encoded by the fusion protein HSA-hLF expression vector pOptiVEC/HSA-hLF is shown as a HSA-hLF sequence (SEQ ID NO: 14). In this HSA-hLF sequence, amino acid positions 1 to 609 (SEQ ID NO: 15) correspond to the amino acid sequence of human serum albumin (HSA) comprising a signal sequence, amino acid positions 610 to 612 (the sequence Leu-Glu-Met) correspond to the amino acid sequence of a spacer, and amino acid positions 613 to 1304 (SEQ ID NO: 16) correspond to the amino acid sequence of human lactoferrin (hLF).

3. Establishment of Cell Lines Stably Expressing the hLF-HSA and HSA-hLF Fusion Proteins For construction of cell lines stably expressing the hLF-HSA and HSA-hLF fusion proteins, DHFR-deficient Chinese hamster ovary cells (DG44), a kind of CHO cells, were used. DHFR refers to dihydrofolate reductase and is essential for biosynthesis of nucleic acids. When cells are cultured in the presence of methotrexate (MTX) serving as an antagonist of DHFR, DHFR production is inhibited. In this state, it is known that the cells amplify the DHFR gene for their survival, as a result of which genes located near the DHFR gene are also amplified and protein expression from these genes is therefore amplified. In this way, a target protein can be highly expressed.

The expression vectors pOptiVEC/hLF-HSA and pOptiVEC/HSA-hLF prepared in Sections 1 and 2 above were linearized by being digested with a restriction enzyme PvuI for their efficient introduction into cells. Electroporation was conducted with a Bio-Rad Gene Pulser Xcell®. CHO (DG44) cells were cultured in ribonucleoside- and deoxyribonucleoside-containing α-MEM medium (product No. 21444, Nacalai Tesque, Inc., Japan) supplemented with 10% FBS. $4.0\times10^5$ cells of these cells were centrifuged to remove the supernatant, and then suspended in 50 μl of PBS. This cell suspension was transferred to a 2 mm gap cuvette for electroporation (Nepa Gene Co., Ltd., Japan), and the linearized vector pOptiVEC/hLF-HSA or pOptiVEC/HSA-hLF was added thereto in an amount of about 13 μg (suspended in 50 μl of PBS). This mixture was subjected to electrical pulses under the conditions "voltage: 160 V, liquid volume: 100 μl, pulse width: 15 msec, interval: 0 s, waveform: square wave" and then allowed to stand for 2 minutes. The whole volume (100 μl) of the mixture was quickly added to 5 ml of ribonucleoside- and deoxyribonucleoside-containing α-MEM medium supplemented with 10% FBS. After centrifugation (200×g for 2 minutes), the pellet was suspended again in 1 ml of ribonucleoside- and deoxyribonucleoside-containing α-MEM medium supplemented with 10% FBS and then transferred to a 12-well cell culture plate. After culture under 5% $CO_2$ at 37° C. for 2 days, the medium was replaced with ribonucleoside- and deoxyribonucleoside-free MEMα medium (product No. 135-15175, Wako Pure Chemical Industries, Ltd., Japan) supplemented with 10% FBS, and culture was continued. The grown cells were scaled up from the 12-well plate to a T75 $cm^2$ flask and cultured therein, followed by gene amplification with methotrexate (MTX, Wako Pure Chemical Industries, Ltd., Japan). After the cells cultured in the T75 $cm^2$ flask were grown to occupy 80% or more of the flask area, the cells were detached with trypsin/EDTA and finally suspended in 10 ml of ribonucleoside- and deoxyribonucleoside-free MEMα medium supplemented with 50 nM MTX and 10% FBS. To a T75 $cm_2$ flask, 1 ml of this cell suspension and 9 ml of fresh ribonucleoside- and deoxyribonucleoside-free MEMα medium supplemented with 50 nM MTX and 10% FBS were added, and the cells were cultured to reach 80% confluency. At stepwise increasing concentrations of MTX (i.e., 500 nM, 1 μM, 2 μM, 3 μM and 4 μM), the cells were also cultured to establish cell lines highly expressing the hLF-HSA and HSA-hLF fusion proteins. The cell lines highly expressing the hLF-HSA and HSA-hLF fusion proteins were designated as DG44(hLF-HSA) cells and DG44 (HSA-hLF) cells, respectively.

4. Large-Scale Expression of the hLF-HSA and HSA-hLF Fusion Proteins

Large-scale expression was conducted by static culture using 175 $cm^2$ T flasks (Greiner). The DG44(hLF-HSA) and DG44(HSA-hLF) cells were cultured in ribonucleoside- and deoxyribonucleoside-free MEMα medium (Wako Pure Chemical Industries, Ltd., Japan) supplemented with 10% FBS to reach 70% confluency. The culture supernatants were removed, and the cells attached to these flasks were washed with PBS, followed by addition of "Hybridoma Serum Free Medium" (trade name, Invitrogen) in 30 ml volumes. The cells were cultured at 37° C. under 5% $CO_2$ for 4 days. After 4 days, the culture supernatants were transferred to 50 ml centrifugal tubes and centrifuged at 10,000×g for 10 minutes, and the supernatants were then transferred to storage containers. To the cells, 30 ml of fresh "Hybridoma Serum Free Medium" (trade name, Invitrogen) was added, and the cells were cultured at 37° C. under 5% $CO_2$ for an additional 4 days to prepare the culture supernatants. After being cultured, the cells were removed by centrifugation and the resulting culture supernatants were each supplemented with sodium azide at a final concentration of 0.02% and stored at 4° C.

5. Purification of the hLF-HSA and HSA-hLF Fusion Proteins

Figure 3:
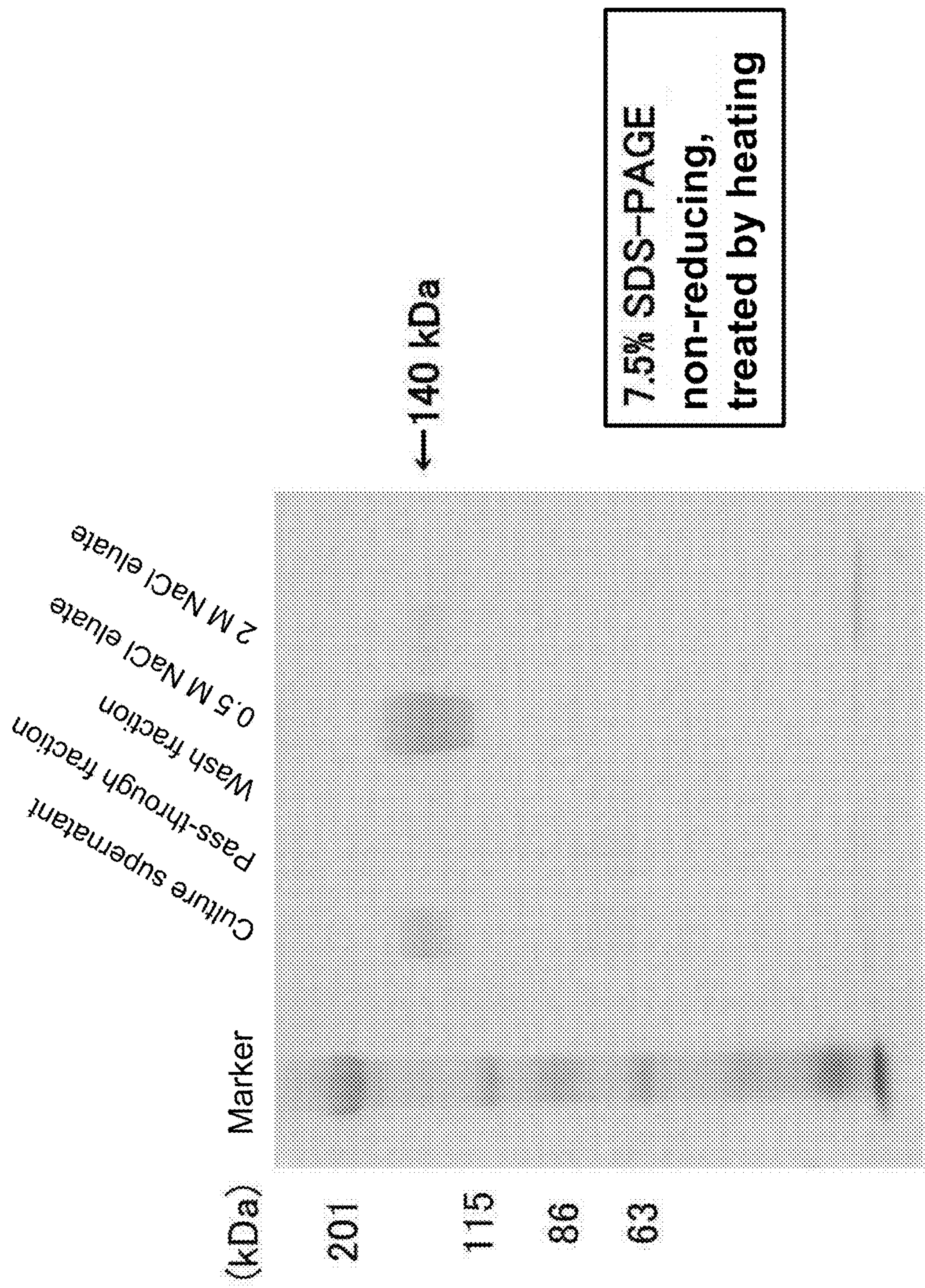
FIG. 3 shows the hLF-HSA fusion protein purified with heparin sepharose 6FF.
Figure 4:
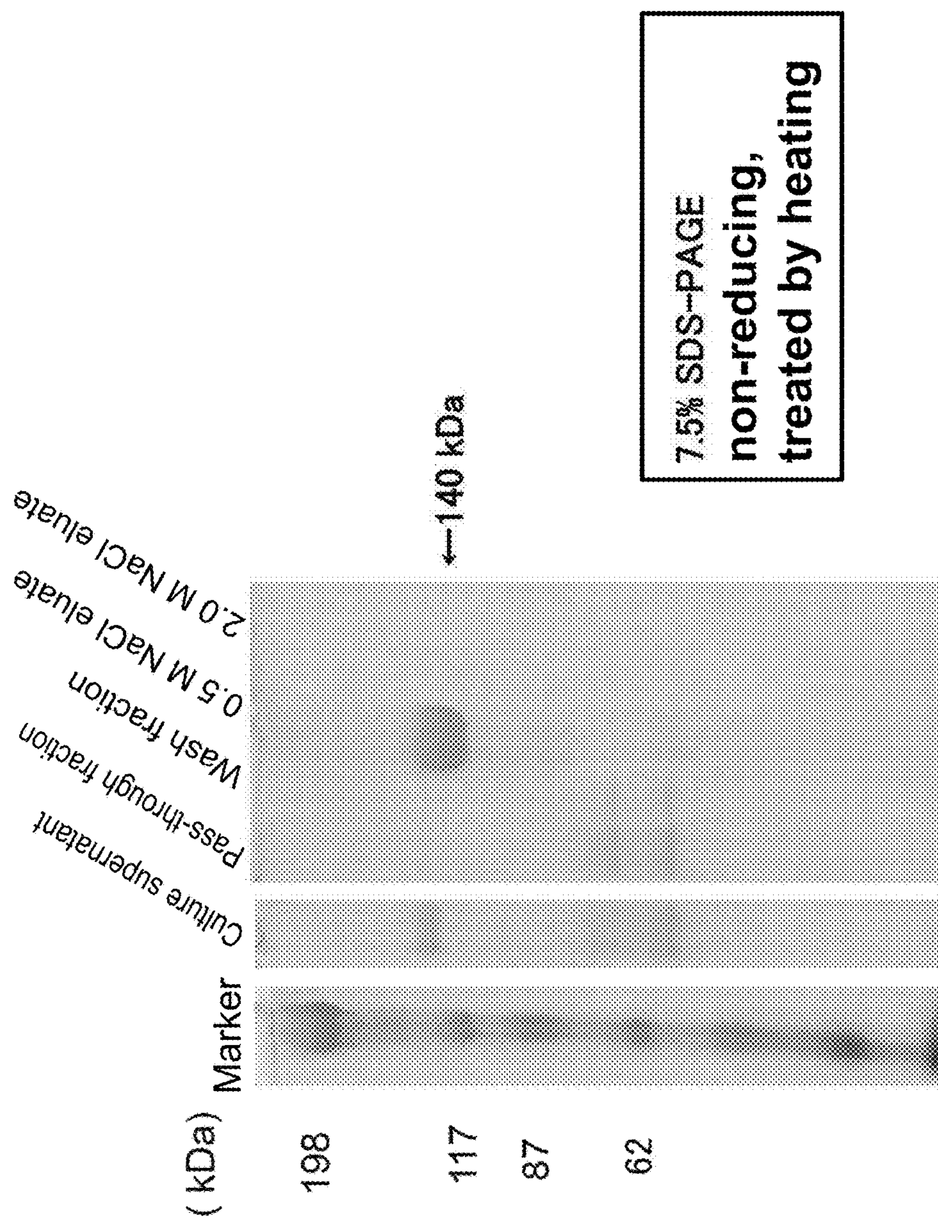
FIG. 4 shows the HSA-hLF fusion protein purified with heparin sepharose 6FF.

For purification, the culture supernatants containing the hLF-HSA and HSA-hLF fusion proteins (each supplemented with sodium azide at a final concentration of 0.02%) obtained by large-scale expression were used directly. Since human lactoferrin (hLF) is known to have the property of strongly binding to heparin, the hLF-HSA and HSA-hLF fusion proteins were purified by affinity purification with Heparin Sepharose 6 Fast Flow (trade name, GE Healthcare). "Poly-Prep Chromatography Columns" (trade name, BioRad Laboratories) were each filled with 2 ml of "Heparin Sepharose 6 Fast Flow" (trade name, GE Healthcare) and equilibrated with 5 column volumes (CV) of 10 mM sodium phosphate buffer (pH 7.0). At 10° C., 500 mL of each culture supernatant was contacted under reflux with the Heparin Sepharose 6 Fast Flow, whereby the fusion protein was adsorbed onto the "Heparin Sepharose 6 Fast Flow." After refluxing, the refluxed culture supernatant was collected as a pass-through fraction. The "Poly-Prep Chromatography Columns" containing a heparin carrier on which the fusion proteins were adsorbed were each connected to a "UV DETECTOR" (Tokyo Rikakikai Co., Ltd., Japan, measured for absorbance at 280 nm) and a microtube pump (Tokyo Rikakikai Co., Ltd., Japan). The flow rate of the pump was set to 1 ml/min, and 10 mM sodium phosphate buffer (pH 7.0) was passed to each column to wash the carrier. From a time point where the absorbance at 280 nm in the "UV DETECTOR" was started to increase, the eluate was collected (wash fraction). This eluate collection was continued until the absorbance at 280 nm was 0. Then, the eluent was replaced with 0.5 M NaCl-containing 10 mM sodium phosphate buffer (pH 7.0), and the same operations were repeated (0.5 M NaCl elution fraction). Further, the eluent was replaced with 2 M NaCl-containing 10 mM sodium phosphate buffer (pH 7.0), and the same operations were repeated (2 M NaCl elution fraction). The collected eluates were each stored at 4° C. 12 μl of each elution fraction was mixed with 4 μl of non-reducing 4× sample buffer, treated by heating at 95° C. for 5 minutes and then analyzed by 7.5% SDS-PAGE. For band staining, CBB was used. The purification results of the hLF-HSA fusion protein are shown in FIG. 3, while the purification results of the HSA-hLF fusion protein are shown in FIG. 4. These fusion proteins both showed no bands in the pass-through and wash fractions, and a band of about 140 kDa was observed for each fusion protein in the 0.5 M NaCl elution fraction. Since no band was observed in the 2 M NaCl elution fraction, the fusion proteins adsorbed onto the Heparin Sepharose 6 Fast Flow were both found to be completely eluted with 0.5 M NaCl. When expressed as described in Section 4 above, the hLF-HSA and HSA-hLF fusion proteins were each found to be obtained in an amount of about 10 to 15 mg as a purified protein from 1 L of the culture supernatant.

Example 2: Measurement of the Iron-Binding Ability of the hLF-HSA Fusion Protein Lactoferrin (LF) is a nonheme iron-binding glycoprotein having a molecular weight of 80,000, which is composed of two regions called N-lobe and C-lobe, and has the ability to form reversible chelate bonds with two iron ions ($Fe^{3+}$) per molecule of protein in the presence of carbonate ions ($CO_3^{2-}$) (Anderson, et al., Nature, 344, 784-78 (1990)). Prior to iron removal operations, the hLF-HSA and HSA-hLF fusion proteins prepared in Sections 4 and 5 above were each measured for the amount of iron ions ($Fe^{3+}$) bound thereto with a "Fe C-Test Wako" (Wako Pure Chemical Industries, Ltd., Japan). As a result, Fe' ions were bound in an amount of 1302 ng for hLF-HSA and 1161 ng for HSA-hLF per mg protein calculated as hLF, which were each almost close to the theoretical value when two iron ions ($Fe^{3+}$) were bound per molecule of protein (i.e., about 1400 ng of $Fe^{3+}$ ions were bound per mg of hLF). Thus, the hLF-HSA and HSA-hLF fusion proteins were both shown to have the ability to bind to iron ions. Further, the iron-binding ability of the hLF-HSA fusion protein was measured in the following manner. From each fusion protein prepared, iron ions ($Fe^{3+}$) were released with phosphate buffer (pH 7.5) containing 10 mM HCl. (pH 2.0) and 0.1% EDTA to prepare apo-form lactoferrin (iron-removed lactoferrin). Then, iron ions ($Fe^{3+}$) were added in the presence of carbonate ions ($CO_3^{2-}$) to prepare iron-rebound lactoferrin. The thus prepared iron-removed lactoferrin and iron-rebound lactoferrin were measured for their iron content and protein concentration to determine the amount of iron bound per mg of hLF protein (in the case of the HSA fusion protein, per mg calculated as hLF using its molecular weight).

More specifically, iron removal was accomplished as follows: *Aspergillus*-derived recombinant hLF (rhLF), human serum albumin (HSA, Wako Pure Chemical Industries, Ltd., Japan) and the hLF-HSA fusion protein were each dialyzed for 24 hours against 10 mM HCl (pH 2.0) and further dialyzed for 24 hours against 100 mM phosphate buffer (pH 7.5) containing 0.1% EDTA and 150 mM NaCl. The samples obtained after iron removal were each regarded as iron-removed lactoferrin. For rebinding of iron, after the above iron removal with hydrochloric acid and EDTA, the samples were dialyzed once for 24 hours against phosphate buffer (pH 7.5) containing 0.001% iron citrate ammonium, 50 mM sodium bicarbonate and 150 mM NaCl and dialyzed once for 24 hours against 50 mM phosphate buffer (pH 6.6) containing 150 mM NaCl to thereby give iron-rebound lactoferrin. For measurement of iron ions bound to the protein, a serum iron measurement kit "Fe C-Test Wako" (trade name, Wako Pure Chemical Industries, Ltd., Japan) was used. The iron-binding ability was calculated as the amount of iron bound per mg of hLF protein quantified by the Bradford assay (in the case of the HSA fusion protein, per mg calculated as hLF using its molecular weight). The hLF-HSA fusion protein was found to retain 100% iron-binding ability when compared to rhLF.

TABLE 1

| | Iron concentration (ng/mg) | | | Relative value (%) assuming that hLF |
|---|---|---|---|---|
| | Iron-removed | Iron-rebound | Holo-Apo | is 100% |
| hLF | 224.0 | 1688.9 | 1465.0 | 100 |
| hLF-HSA | 590.0 | 2341.7 | 1751.6 | 119.6 |

Example 3: CD Spectral Study on the Thermal Stability of the hLF-HSA and HSA-hLF Fusion Proteins The HSA-hLF and hLF-HSA fusion proteins were analyzed for their thermal stability by circular dichroism (CD)

spectrometry. The circular dichroism (CD) spectrometry is a technique to measure a difference in absorbance between right-handed circularly polarized light and left-handed circularly polarized light when a substance is irradiated at a certain wavelength. This technique can be used to predict the presence or absence, type and content of protein secondary structure.

Figure 5:
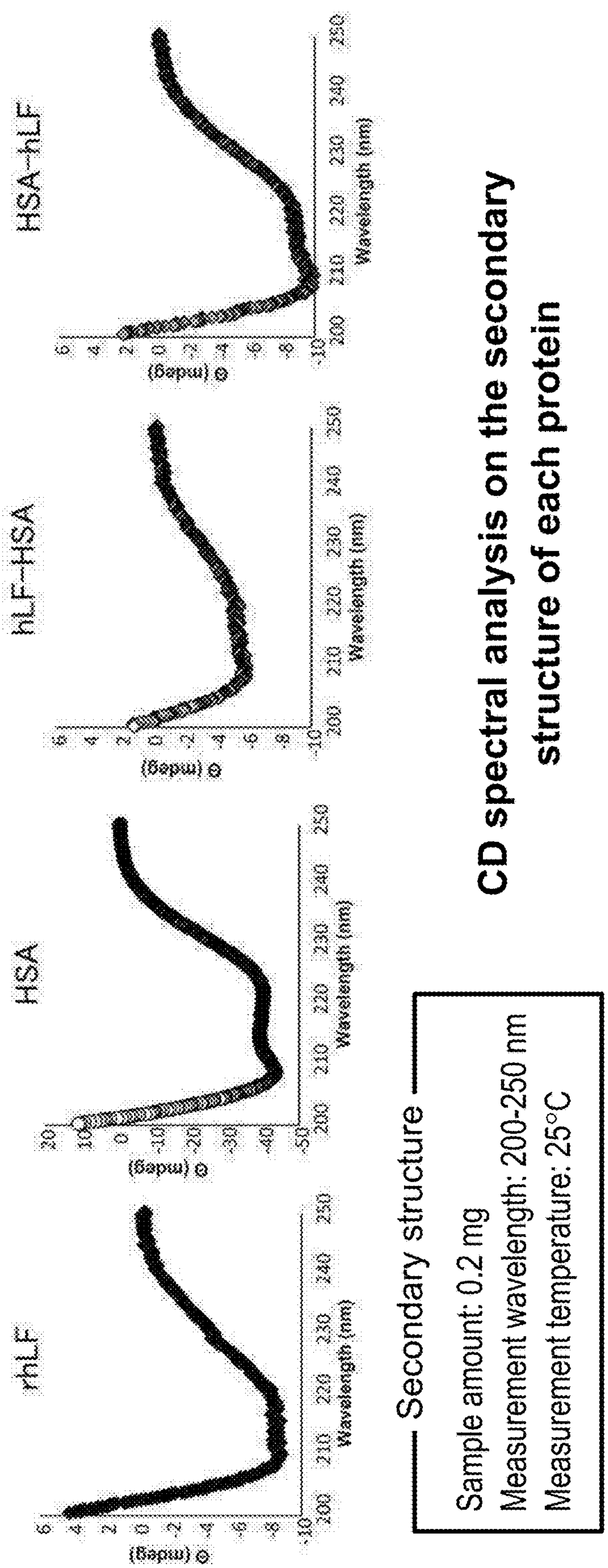
FIG. 5 shows the CD spectra obtained for *Aspergillus*-derived recombinant hLF (rhLF), human serum albumin (HSA) and the hLF-HSA and HSA-hLF fusion proteins.
Figure 6:
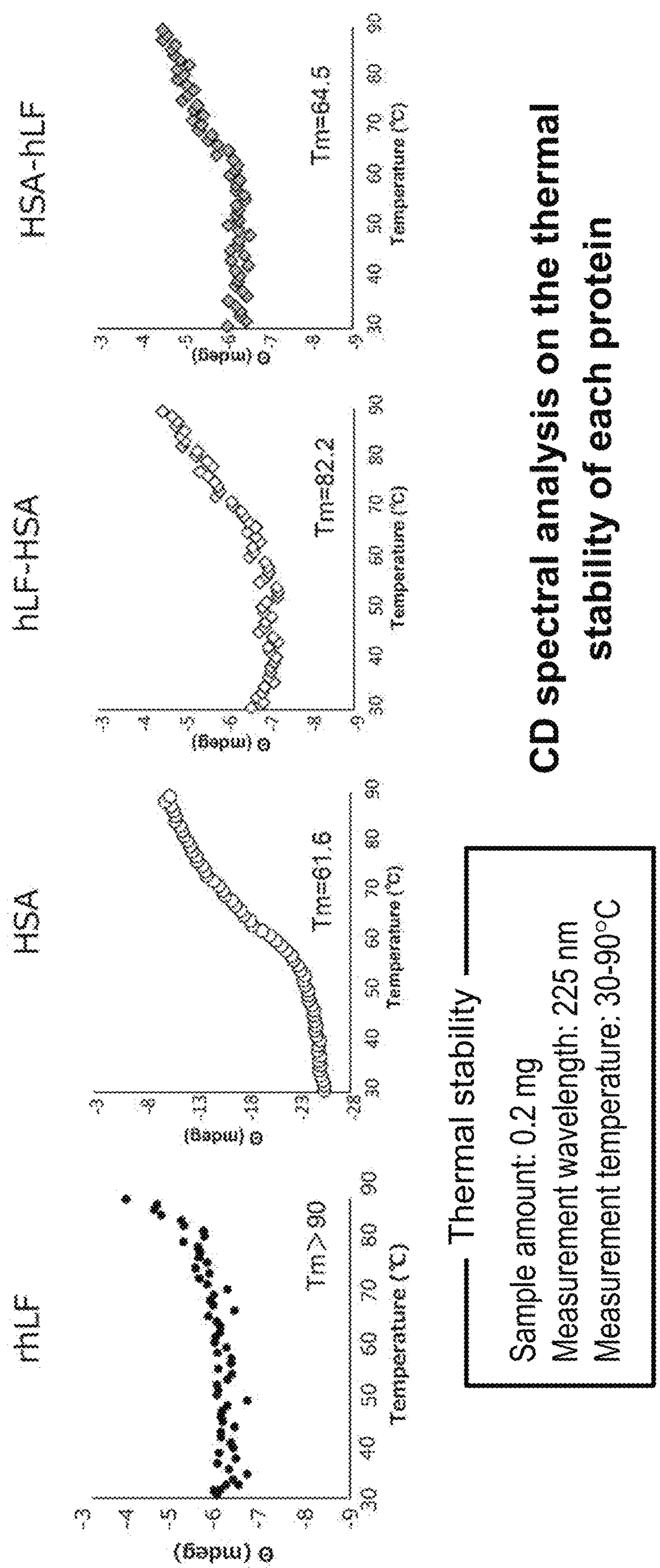
FIG. 6 shows the thermal stability of *Aspergillus*-derived recombinant hLF (rhLF), human serum albumin (HSA) and the hLF-HSA and HSA-hLF fusion proteins, as analyzed by their CD spectra.

First, suspensions of *Aspergillus*-derived recombinant hLF (rhLF), human serum albumin (HSA, Wako Pure Chemical Industries, Ltd., Japan) and the hLF-HSA and HSA-hLF fusion proteins were prepared at 0.1 mg/ml in PBS(−) and measured for their CD spectra at 25° C. at a wavelength of 200 nm to 250 nm (using a circular dichroism spectropolarimeter J-1500, JASCO Corporation, Japan). The results obtained are shown in FIG. 5. The HSA-hLF and hLF-HSA fusion proteins were both confirmed for their secondary structure, and there was no significant change in the secondary structure of hLF upon fusion between hLF and HSA. Then, thermal stability was studied for each protein. When a CD spectrum is measured while varying the temperature of a protein solution from low temperature to high temperature, [θ] is increased to reach a plateau at a certain temperature. This phenomenon is due to heat-induced denaturation of the protein and the subsequent change in the secondary structure of the protein. For monitoring of thermal stability, the wavelength commonly used for measurement is around 225 nm. Suspensions of *Aspergillus*-derived recombinant hLF (rhLF), human serum albumin (HSA, Wako Pure Chemical Industries, Ltd., Japan) and the hLF-HSA and HSA-hLF fusion proteins were prepared at 0.1 mg/ml in PBS(−) and measured for their CD spectra at a wavelength of 225 nm while increasing the temperature from 30° C. to 90° C. in increments of 1° C. (using a circular dichroism spectropolarimeter J-1500, JASCO Corporation, Japan). The denaturation temperature (Tm) upon change in the secondary structure was calculated using the thermal denaturation analysis program Spectra Manager Ver. 2 (JASCO Corporation, Japan). It should be noted that since it has been reported that hLF shows higher thermal stability when a larger amount of iron is bound thereto (Spreedhara, A. et al., Biometals 23, 1159-1170, 2010), the iron content in the samples used in this study were measured with a "Fe C-Test Wako" (trade name, Wako Pure Chemical Industries, Ltd., Japan). As a result, substantially the same amount of iron was bound to each sample, i.e., 1222 ng/mg for rhLF, 1302 ng/mg for hLF-HSA and 1161 ng/mg for HSA-hLF. The results obtained for the thermal stability of each protein are shown in FIG. 6. The denaturation temperature (Tm) of each protein was 90° C. or higher for rhLF, 61.6° C. for HSA, 82.2° C. for hLF-HSA and 64.5° C. for HSA-hLF, thus indicating that the Tm values of the fusion proteins were both lower than that of rhLF, but the hLF-HSA fusion protein was found to retain higher thermal stability than HSA-hLF.

Figure 7:
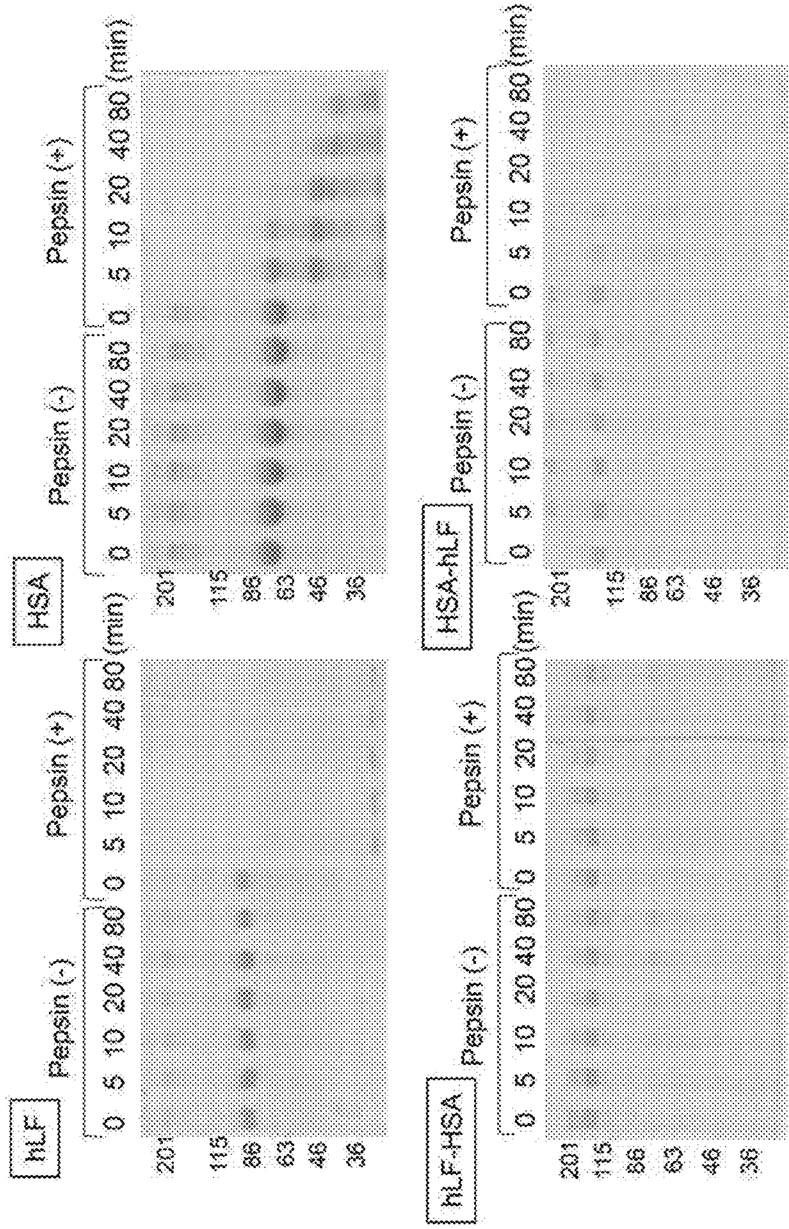
FIG. 7 shows the pepsin resistance of *Aspergillus*-derived recombinant hLF (rhLF), human serum albumin (HSA) and the hLF-HSA and HSA-hLF fusion proteins, as analyzed by SDS-PAGE.
Figure 8:
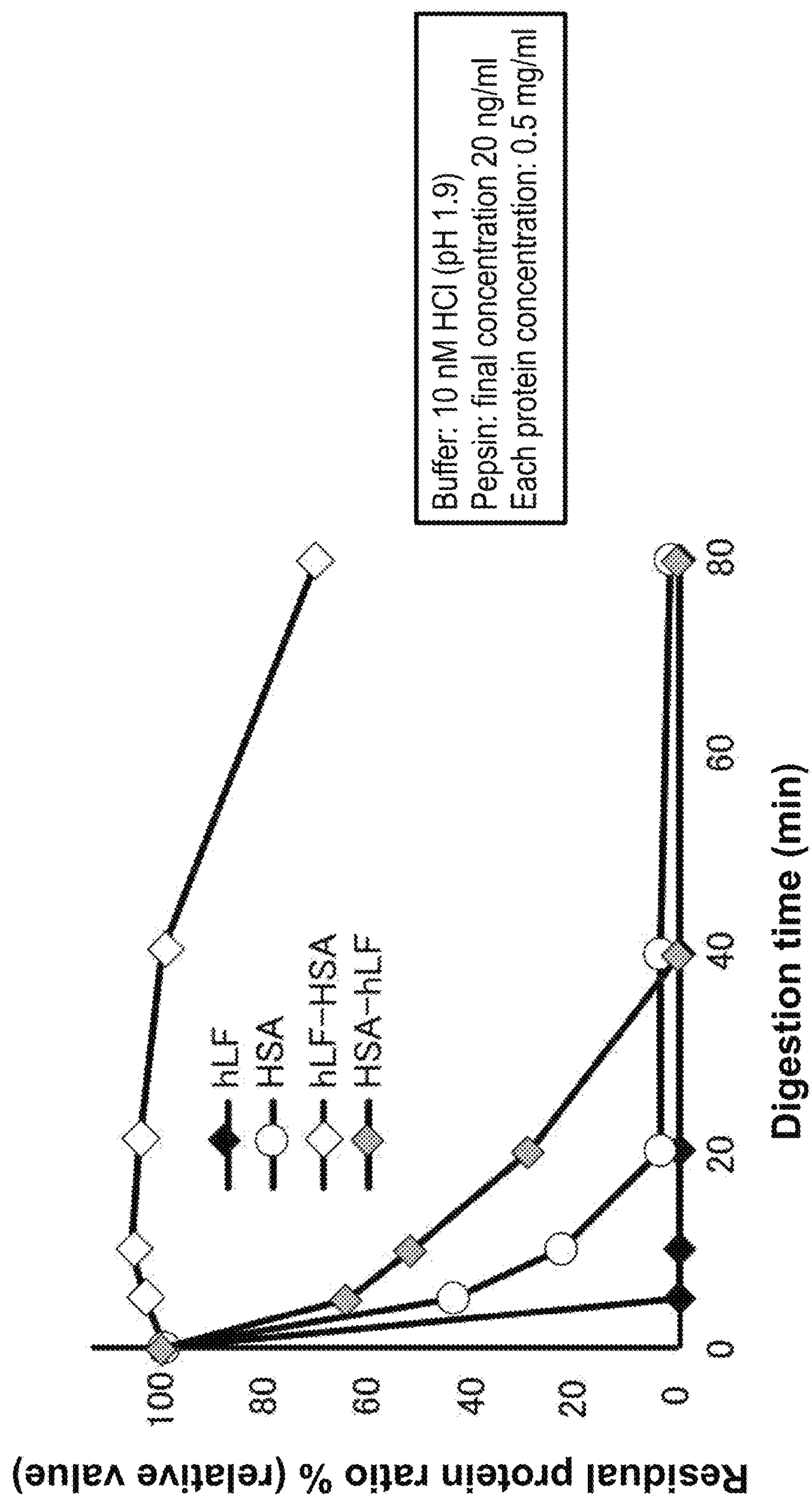
FIG. 8 shows the pepsin resistance of *Aspergillus*-derived recombinant hLF (rhLF), human serum albumin (HSA) and the hLF-HSA and HSA-hLF fusion proteins, as analyzed by SDS-PAGE (FIG. 7), followed by densitometer analysis of their band densities. The results are presented in graphical form.

Example 4: Pepsin Digestion Resistance of the HSA-hLF and hLF-HSA Fusion Proteins Protein solutions (*Aspergillus*-derived recombinant hLF (rhLF), human serum albumin (HSA, Wako Pure Chemical Industries, Ltd., Japan) and the hLF-HSA and HSA-hLF fusion proteins) were each adjusted to a concentration of 1.2 mg/ml, and 35 μl of each protein solution was mixed with 40.6 μl of 10 mM HCl (pH 2.0) and then allowed to stand at 37° C. for 5 minutes. Subsequently, 8.4 μl of a 200 ng/ml pepsin solution (Wako Pure Chemical Industries, Ltd., Japan; a solution of pig stomach pepsin in 10 mM HCl (pH 2.0)) was added to initiate the digestion reaction. Reaction samples (12 μl each) were collected over time and each added to 4 μl of reducing 4× Sample Buffer prepared in advance (0.1 M Tris-HCl (pH 6.8), 8% SDS, 40% glycerol, 20% 2-mercaptoethanol, 0.1% BPB) to stop the digestion reaction. Subsequently, the samples were subjected to thermal treatment at 95° C. for 5 minutes, 4 μl aliquots of which were then electrophoresed by 7.5% SDS-PAGE. The gels were stained with CBB. FIG. 7 shows the results of electrophoresis obtained for, from the left, samples in which each protein was allowed to stand at 37° C. for 0, 5, 10, 20, 40 and 80 minutes in the absence of pepsin (expressed as Pepsin (−)), and samples in which each protein was allowed to stand at 37° C. for 0, 5, 10, 20, 40 and 80 minutes in the presence of pepsin (expressed as Pepsin (+)). The density of each band was analyzed with CS Analyzer (ATTO) software for scoring the density of the stained band. Assuming that the band density of each protein at a digestion time of 0 minutes was set to 100%, the relative densities were plotted on a graph (FIG. 8). hLF serving as a control was completely degraded within 5 minutes, whereas the hLF-HSA and HSA-hLF fusion proteins were both resistant to digestion. The degradation half-life of each protein upon pepsin digestion was calculated to be 5 minutes or less for hLF, 3.1 minutes for HSA, 80 minutes or more for hLF-HSA and 9.3 minutes for HSA-hLF, thus indicating that particularly hLF-HSA was remarkably resistant to pepsin digestion.

Example 5: Intracellular Uptake into Human Small Intestinal Epithelium-Like Cells Caco-2 and Extracellular Release Therefrom LF is known to be taken up in an intact molecular form through the intestinal tract, transferred in an intact molecular form to the thoracic duct lymph, and then distributed throughout the body from the vena cava (Takeuchi et al., Exp Physiol., Vol. 89, 263-270, 2004). Moreover, intracellular LF uptake into human small intestinal epithelium-like cells Caco-2 and extracellular LF release therefrom are considered to be phenomena mimicking LF absorption in the intestinal tract. Then, *Aspergillus*-derived recombinant hLF (rhLF) and the hLF-HSA and HSA-hLF fusion proteins were each labeled with a fluorescent probe and reacted with Caco-2 cells, and their uptake within the cells was observed under a confocal laser scanning microscope. In addition, each non-labeled protein was taken up into Caco-2 cells, and cell lysates were then prepared from the Caco-2 cells, followed by Western blotting with polyclonal antibody against LF to analyze the state of each protein within the cells. Further, after each non-labeled protein was taken up into Caco-2 cells, each protein released from the cells was analyzed by Western blotting with polyclonal antibody against hLF.

1. Intracellular Uptake Observation Under a Confocal Laser Scanning Microscope

Each protein was labeled with a fluorescent probe, Alexa Fluor® 488 (Thermo Fisher Scientific). After 1 mg of Alexa Fluor® 488 was diluted with 100 μl of DMSO, each protein supplemented with 1 M $NaHCO_3$ and the thus prepared Alexa Fluor® 488 were mixed at a molar ratio of 1:10 and reacted at room temperature for 1 hour. After the reaction, the reaction solution was dialyzed against 1×PBS(−) for 24 hours to remove free Alexa Fluor® 488 which was not bound to the protein, thereby giving the protein labeled with Alexa Fluor®488.

Caco-2 cells were seeded in 12-well plates at a cell density of $5\times10^4$ cells/ml and cultured at 37° C. under 5%

Figure 9:
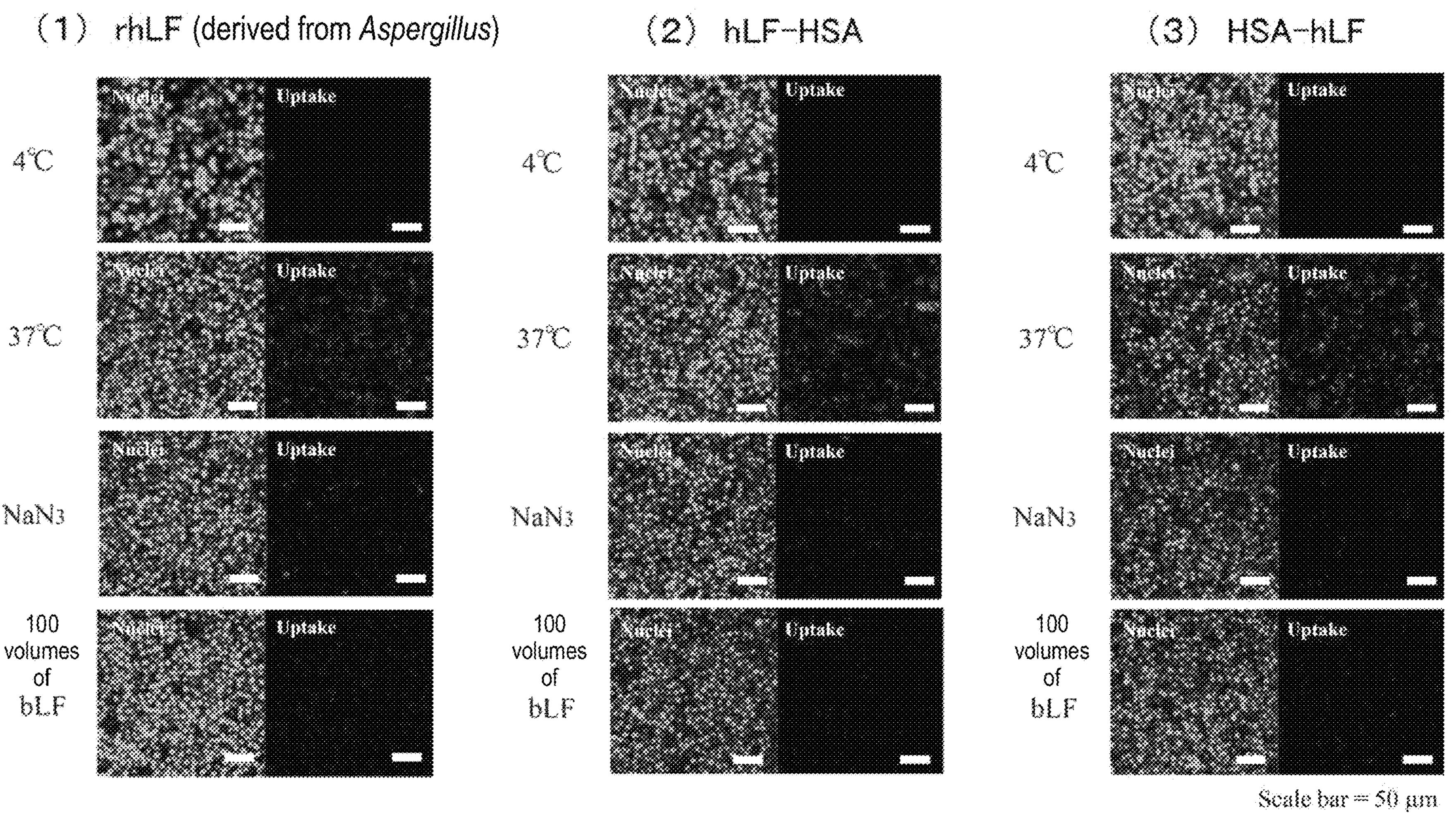
FIG. 9 shows the intracellular uptake of *Aspergillus*-derived recombinant hLF (rhLF) and the hLF-HSA and HSA-hLF fusion proteins, each being fluorescently labeled, into human small intestinal epithelium-like cells Caco-2, as analyzed with a confocal laser scanning microscope.

$CO_2$ for 1 week with medium replacement every 2 days. To the Caco-2 cells, PBS(−) was added at 500 μl/well, and washing was repeated three times for complete removal of the medium components. Then, each Alexa-labeled protein suspended in PBS(−) was added at 15 μg/well and reacted at 4° C. and 37° C. for 1 hour. For reaction at 37° C., additional cases were also tested where $NaN_3$ serving as an ATP synthesis inhibitor was added at a final concentration of 0.2% and where 150 μg of non-labeled bovine lactoferrin (bLF) was added. After 1 hour, each Alexa-labeled protein was removed, and the cells were washed once by addition of cold PBS(−) at 500 μl/well. After washing, 0.25% Trypsin/EDTA was added at 200 μl/well and reacted at room temperature for 3 minutes to detach the cells from the plates. All the cells were collected into centrifugal tubes, washed with cold PBS(−) and then treated with 4% PFA/PBS(−) for 15 minutes to fix the cells. The cells were washed again with cold PBS(−), and a 1 μg/ml bisbenzimide (Bisbenzimide H33258 Trihydrochloride, Wako Pure Chemical Industries, Ltd., Japan) solution suspended in PBS(−) was added thereto at 200 μl/tube, followed by reaction at room temperature for 30 minutes to stain their nuclei. After being washed with cold PBS(−), all the cells were transferred to a 8-well chamber plate and observed for fluorescence taken up thereby under a confocal laser scanning microscope LSM510 (Carl Zeiss). The results confirmed that rhLF and the hLF-HSA and HSA-hLF fusion proteins were not taken up into Caco2 cells under conditions of 4° C. (FIG. 9, 4° C.), but were taken up into Caco2 cells under conditions of 37° C. (FIG. 9, 37° C.). Moreover, their uptake at 37° C. was completely inhibited by addition of $NaN_3$ serving as an ATP synthesis inhibitor (FIG. 9, $NaN_3$) and 100 volumes of unlabeled bLF relative to the labeled protein (FIG. 9, 100 volumes of bLF), thus suggesting that this intracellular uptake was receptor-mediated and the hLF-HSA and HSA-hLF fusion proteins were taken up into the cells through the same uptake route as LF. Namely, the hLF-HSA and HSA-hLF fusion proteins are considered to be taken up via any one or more of the lactoferrin receptor or the albumin receptor, each being expressed in Caco2 cells.

Figure 10:
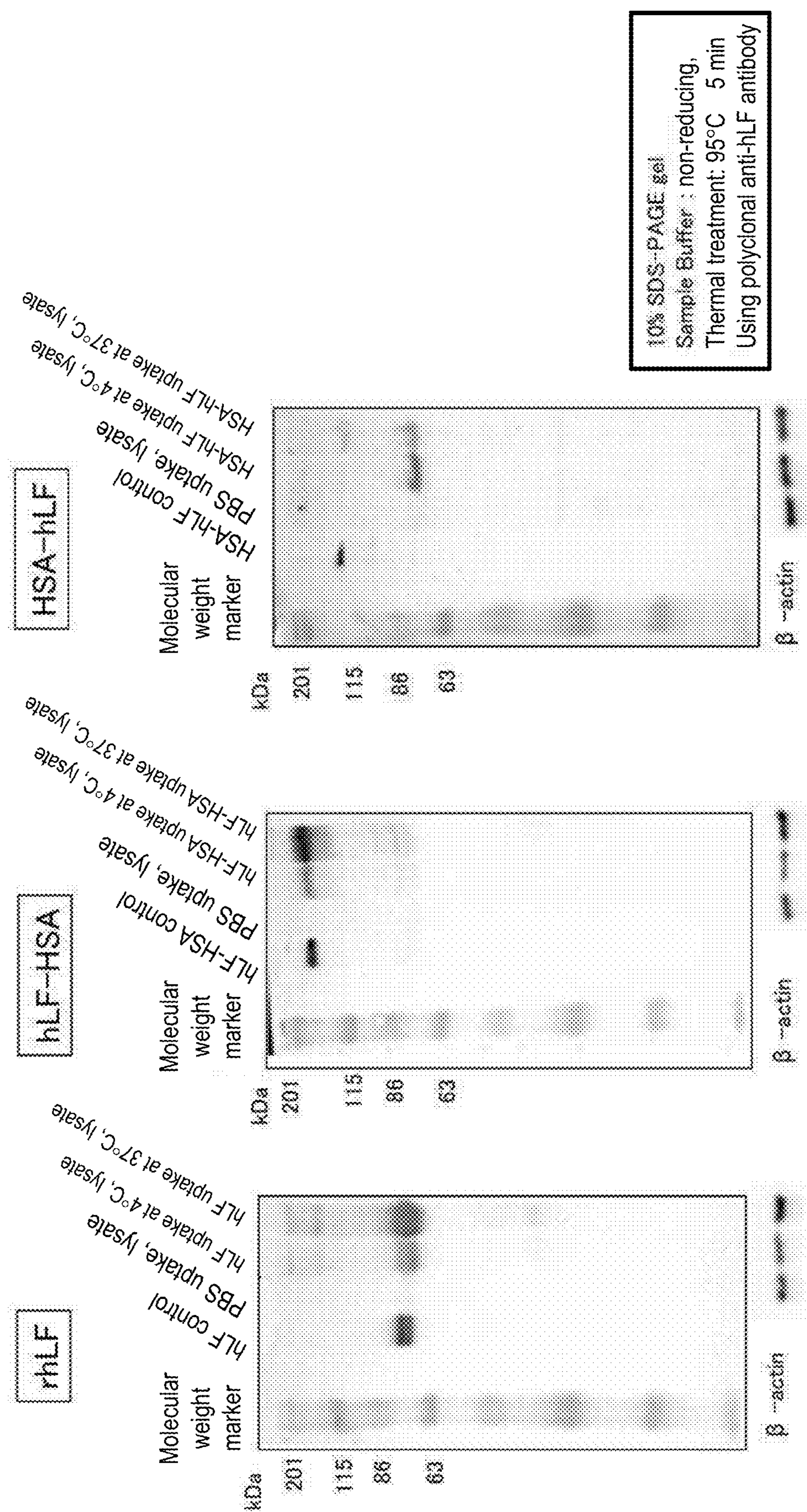
FIG. 10 shows the intracellular uptake of *Aspergillus*-derived recombinant hLF (rhLF) and the hLF-HSA and HSA-hLF fusion proteins into human small intestinal epithelium-like cells Caco-2, as analyzed by Western blotting with polyclonal antibody against hLF.

2. Intracellular Uptake Analysis by Western Blotting with Polyclonal Anti-hLF Antibody Caco-2 cells were seeded in 12-well plates at a cell density of $5\times10^4$ cells/ml and cultured at 37° C. under 5% $CO_2$ for 1 week with medium replacement every 2 days. To the Caco-2 cells, PBS(−) was added at 500 μl/well, and washing was repeated three times for complete removal of the medium components. Then, each protein suspended in PBS(−) was added at 15 μg/well and reacted at 4° C. and 37° C. for 1 hour. After the reaction, cold PBS(−) was added at 500 μl/well, and washing was repeated three times. After washing, 0.25% Trypsin/1 mM EDTA was used to detach the cells from the plates, and the cells were collected into 1.5 ml centrifugal tubes. The cells were washed by addition of cold PBS(−) at 500 μl/ml, followed by centrifugation at 200×g for 2 minutes at 4° C. to collect the cells. This washing operation was repeated three times, and the cells were finally crushed by being reacted at 4° C. for 30 minutes with 100 μl of cold Lysis buffer (a PBS(−) solution containing 1% Triton X-100 and protein inhibitors). Subsequently, centrifugation was conducted at 18,700×g for 15 minutes at 4° C. to collect the supernatant as a cell lysate. Using 10% SDS-PAGE, each cell lysate in an amount of 36 μg per lane was electrophoresed under non-reducing conditions. After electrophoresis, the protein in each lane was transferred onto a nitrocellulose blotting membrane (Protran® Premium 0.45 μm NC, GE Healthcare) in a standard manner and then reacted with Human Lactoferrin antibody (Rabbit polyclonal, A80-144A, Betheyl) as a primary antibody and with Anti Rabbit IgG(Fc), Monoclonal Antibody, Peroxidase Conjugated, 016-23943, Wako Pure Chemical Industries, Ltd., Japan) as a secondary antibody. Band detection was accomplished by chemiluminescence techniques (Immunozeta, Wako Pure Chemical Industries, Ltd., Japan). As a result, rhLF taken up into the cells at 37° C. was detected as an intact molecule at the same position as control rhLF. On the other hand, the band detected was less dense in rhLF reacted with the cells at 4° C. than in rhLF reacted with the cells at 37° C. (FIG. 10, rhLF in the left panel). As in the case of rhLF, hLF-HSA taken up into the cells at 37° C. was detected as an intact molecule at the same position as control hLF-HSA. On the other hand, the band detected was less dense in hLF-HSA reacted with the cells at 4° C. than in hLF-HSA reacted with the cells at 37° C. (FIG. 10, hLF-HSA in the middle panel). The foregoing results confirmed that hLF-HSA was taken up in an intact state into Caco2 cells, as in the case of rhLF. On the other hand, in the case of HSA-hLF having a molecular weight of about 140 kDa, a band was detected primarily at a position of about 80 kDa upon reaction with the cells at 37° C. (FIG. 10, HSA-hLF in the right panel). This infers that when HSA-hLF was taken up into the cells, the binding site between HSA and hLF was cleaved, whereby hLF of 80 kDa was detected with an anti-hLF antibody. Thus, HSA-hLF was found to be degraded when taken up into Caco2 cells.

Figure 11:
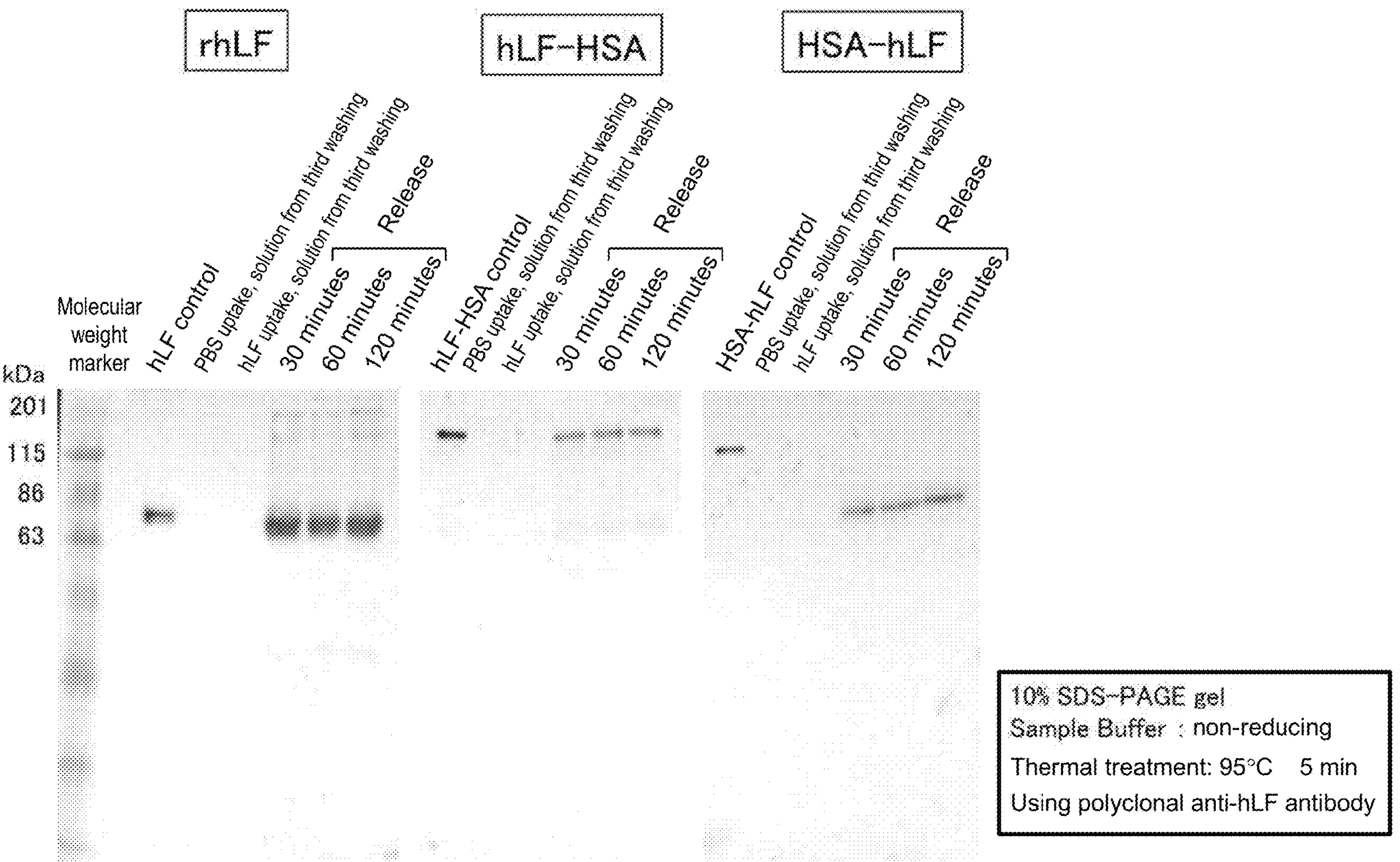
FIG. 11 shows the uptake of *Aspergillus*-derived recombinant hLF (rhLF) and the hLF-HSA and HSA-hLF fusion proteins into human small intestinal epithelium-like cells Caco-2 and their subsequent extracellular release, as analyzed by Western blotting with polyclonal antibody against hLF.

3. Extracellular Release Analysis by Western Blotting with Polyclonal Anti-hLF Antibody Caco-2 cells were seeded in 12-well plates at a cell density of $5\times10^4$ cells/ml and cultured at 37° C. under 5% $CO_2$ for 1 week with medium replacement every 2 days. To the Caco-2 cells, PBS(−) was added at 500 μl/well, and washing was repeated three times for complete removal of the medium components. Then, each protein suspended in PBS(−) was added at 15 μg/well and reacted at 37° C. for 1 hour. After the reaction, cold PBS(−) was added at 500 μl/well, and washing was repeated three times. After washing, 0.25% Trypsin/1 mM EDTA was used to detach the cells from the plates, and the cells were collected into 1.5 ml centrifugal tubes. The cells were washed three times by addition of cold PBS(−) (1 ml), followed by centrifugation at 200×g for 2 minutes at 4° C. to collect the cells (the solution from the third washing was analyzed by Western blotting). The cells were suspended in 200 μl of D-MEM medium (Wako Pure Chemical Industries, Ltd., Japan) and reacted at 37° C. for 30, 60 and 120 minutes to release each protein into the medium. The medium was centrifuged at 6000 rpm for 10 minutes, and the supernatant was analyzed by Western blotting with polyclonal antibody against hLF. Western blotting was accomplished in the same manner as described above for intracellular uptake. The results obtained are shown in FIG. 11. rhLF was released in its 80 kDa intact state into the medium. Likewise, hLF-HSA was also released in an intact state into the medium, as in the case of rhLF. On the other hand, in the case of HSA-hLF for which the binding site between HSA and hLF was suggested to be cleaved during intracellular uptake, hLF alone was released into the medium.

Example 6: Study on the Blood Stability of the hLF-HSA and HSA-hLF Fusion Proteins in Rats Under anesthesia with pentobarbital sodium, a cannula for blood collection was kept in the external jugular vein of each of five Wistar rats (male) at 8 weeks of age. The rats were administered with the hLF-HSA or HSA-hLF fusion protein at a dose of 1 mg/kg body weight calculated as hLF by injection into the femoral vein. Before administration and at 1, 5, 10, 15, 30, 60, 120, 180 and 240 minutes after administration, blood was sampled via the cannula kept in the external jugular vein, and the hLF concentration in plasma was measured by ELISA ("AssayMax Human Lactoferrin ELISA kit," Assaypro). It should be noted that preliminary studies have been conducted to confirm that neither the anticoagulant EDTA used during blood collection nor plasma affects this ELISA measurement.

First, the hLF-HSA and HSA-hLF fusion proteins of known concentration were used to prepare their respective calibration curves by the Bradford assay. Since linearity was obtained at 0.24 to 15.0 ng/ml for both the hLF-HSA and HSA-hLF fusion proteins, each plasma sample was diluted such that its measured value fell within this range, and then measured for its protein concentration.

Figure 12:
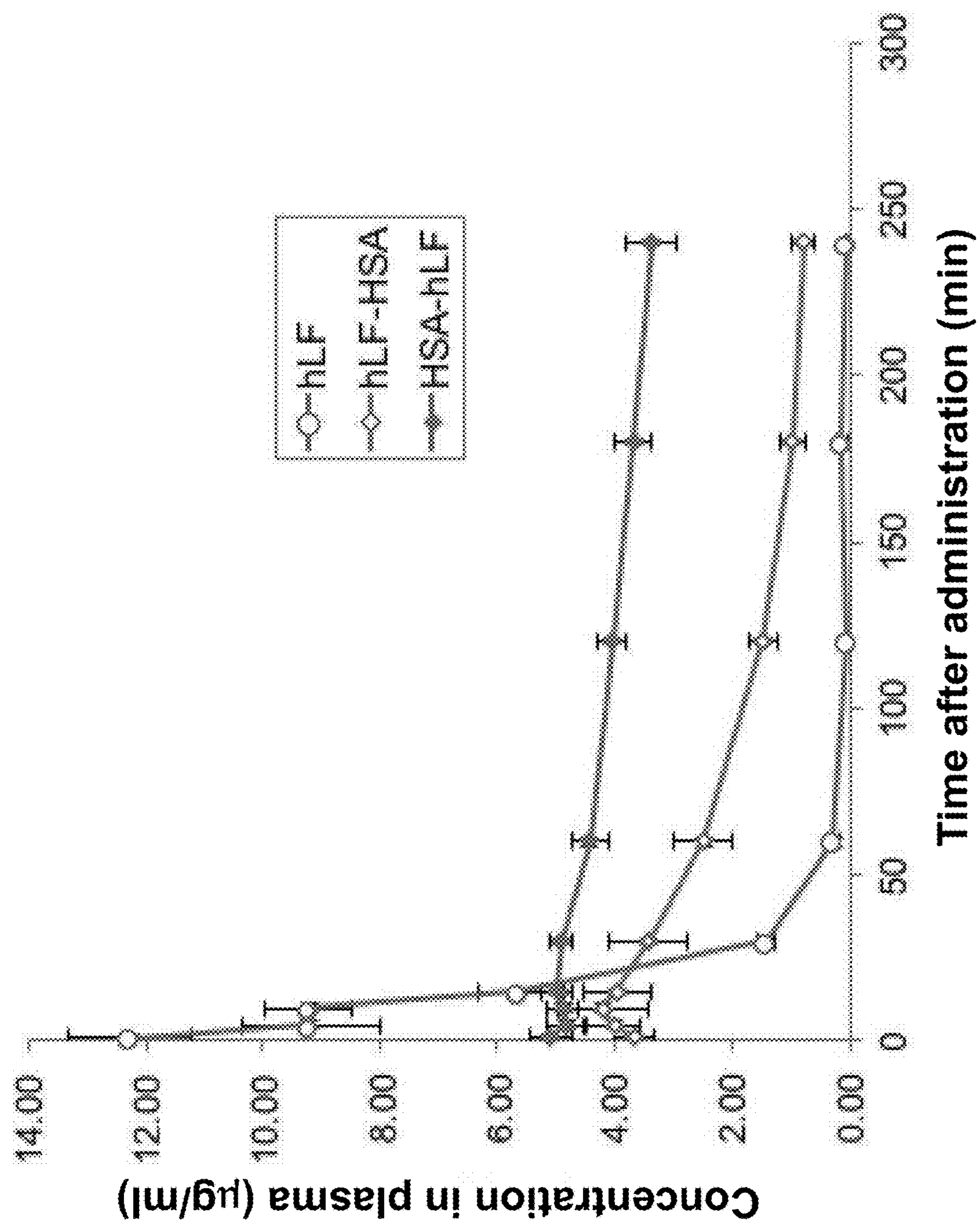
FIG. 12 shows the blood stability of both hLF-HSA and HSA-hLF fusion proteins in rats (rhLF data were quoted from Shiga, Y et al., Eur J Pharm Sci. Vol. 67, 136-143, 2015).

The results obtained are shown in FIG. 12, along with the blood level profile of rhLF measured previously in the same manner. Before administration, LF was not detected in blood from both groups receiving the hLF-HSA and HSA-hLF fusion proteins. The blood level of rhLF remained high until 15 minutes after administration, but thereafter the level was rapidly decreased, so that the blood levels of the fusion proteins were higher than that of rhLF. In particular, the blood level of HSA-hLF was high.

Figure 13:
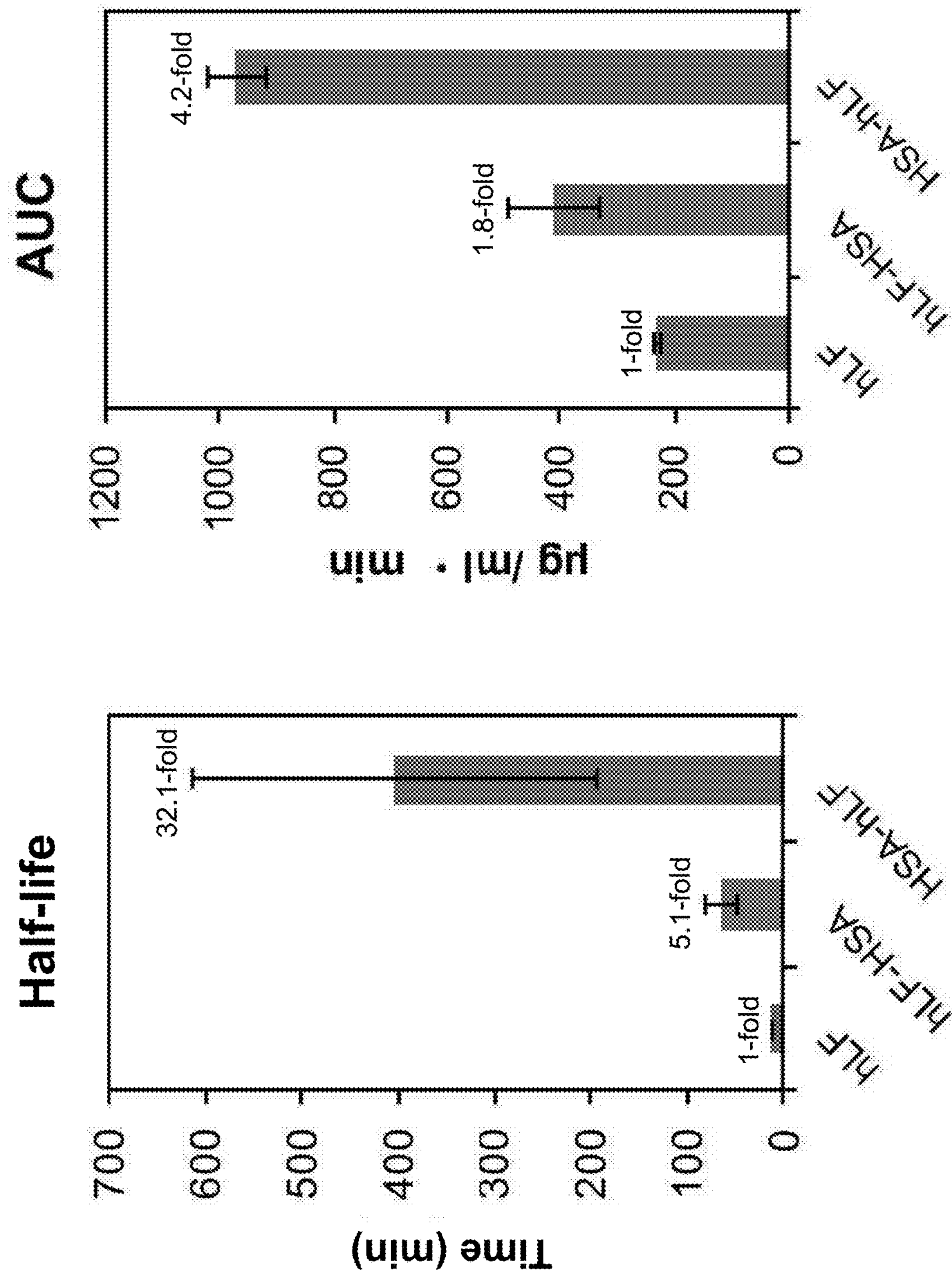
FIG. 13 shows the half-life and AUC values of both hLF-HSA and HSA-hLF fusion proteins in rats. The numerical values in each graph represent the relative values of both hLF-HSA and HSA-hLF fusion proteins, based on the value of hLF.

Statistical analysis software "GraphPad Prism® 4" (GraphPad Software) was used to calculate the half-life in blood and the area under the time curve (AUC). The half-life in the group receiving *Aspergillus*-derived recombinant hLF was 12.6 minutes, whereas the half-life was 64 minutes and 404 minutes in the groups receiving the hLF-HSA and HSA-hLF fusion proteins, respectively, i.e., was prolonged about 5.1-fold and 32.1-fold in comparison with the group receiving hLF (FIG. 13). AUC was increased about 1.8-fold and 4.2-fold in the groups receiving the hLF-HSA and HSA-hLF fusion proteins, respectively, in comparison with the group receiving hLF, thus indicating that their blood stability was remarkably improved.

The results of in vitro pepsin digestion resistance and thermal stability analysis by CD spectrometry indicated that the hLF-HSA and HSA-hLF fusion proteins both showed an improvement in molecular stability when compared to rhLF. In particular, hLF-HSA showed a significant improvement in molecular stability when compared to HSA-hLF. On the other hand, the in vivo results indicated that the hLF-HSA and HSA-hLF fusion proteins both showed an improvement in blood stability when compared to rhLF. In particular, the HSA-hLF fusion protein showed a significant improvement in blood stability when compared to hLF-HSA. These results indicate difficulties in predicting the effect obtained depending on the position at which HSA is fused, i.e., depending on whether HSA is fused at the N-terminal side or at the C-terminal side of hLF.

Example 7: Measurement of the Iron-Binding Ability of the hLF-HSA and HSA-hLF Fusion Proteins (Iron Removal and Iron Rebinding with Sodium Thiocyanate and EDTA)

Prior to iron removal operations, the hLF-HSA and HSA-hLF fusion proteins prepared in the same manner as shown in Sections 4 and 5 above as well as rhLF were each measured for the amount of iron ions ($Fe^{3+}$) bound thereto with a "Fe C-Test Wako" (Wako Pure Chemical Industries, Ltd., Japan). As a result, $Fe^{3+}$ ions were bound in an amount of 1207 ng for hLF-HSA, 819 ng for HSA-hLF and 1966 ng for rhLF per mg protein calculated as hLF. Since HSA-hLF will be precipitated under acidic conditions, the method of iron removal with hydrochloric acid shown in Section 6 above is not suitable. For this reason, for iron removal under neutral conditions, an attempt was made to use sodium thiocyanate which is a chaotropic salt. To solutions of rhLF and the hLF-HSA and HSA-hLF fusion proteins, sodium thiocyanate was added at a final concentration of 5 M and EDTA was added at a final concentration of 0.1%, followed by incubation at room temperature for 16 hours. Subsequently, these solutions were each dialyzed for 24 hours against 50 mM phosphate buffer (pH 6.6) containing 150 mM NaCl to accomplish iron removal. For rebinding of iron, after iron removal, the solutions were each dialyzed once for 24 hours against phosphate buffer (pH 7.5) containing 0.001% iron citrate ammonium, 50 mM sodium bicarbonate and 150 mM NaCl and dialyzed once for 24 hours against 50 mM phosphate buffer (pH 6.6) containing 150 mM NaCl to thereby give iron-rebound lactoferrin. For measurement of iron ions bound to each protein, a serum iron measurement kit "Fe C-Test Wako" (trade name, Wako Pure Chemical Industries, Ltd., Japan) was used. The iron-binding ability was calculated as the amount of iron bound per mg of hLF protein quantified by the Bradford assay (in the case of the HSA fusion proteins, per mg calculated as hLF using their molecular weight). The results obtained are shown in the table below. Assuming that the binding activity of rhLF was set to 100%, the rhLF-HSA and rHSA-hLF fusion proteins showed 147% and 69.5% iron-binding ability, respectively.

TABLE 2

Iron removal and iron rebinding with 5M sodium thiocyanate and 0.1% EDTA (n = 3)

| | Concentration of iron bound (ng/mg calculated as hLF) | | | | |
|---|---|---|---|---|---|
| | Initial amount of iron bound to protein | Apo | Holo | Holo − Apo | Relative amount assuming that the amount bound to rhLF is 100% |
| rhLF | 1966 | 1166 ± 643 | 2004 ± 301 | 838 | 100 |
| hLF-HSA | 1207 | 413 ± 123 | 1645 ± 129 | 1232 | 147 |
| HSA-hLF | 819 | 651 ± 83 | 1233 ± 68 | 582 | 69.5 |

Figure 14:
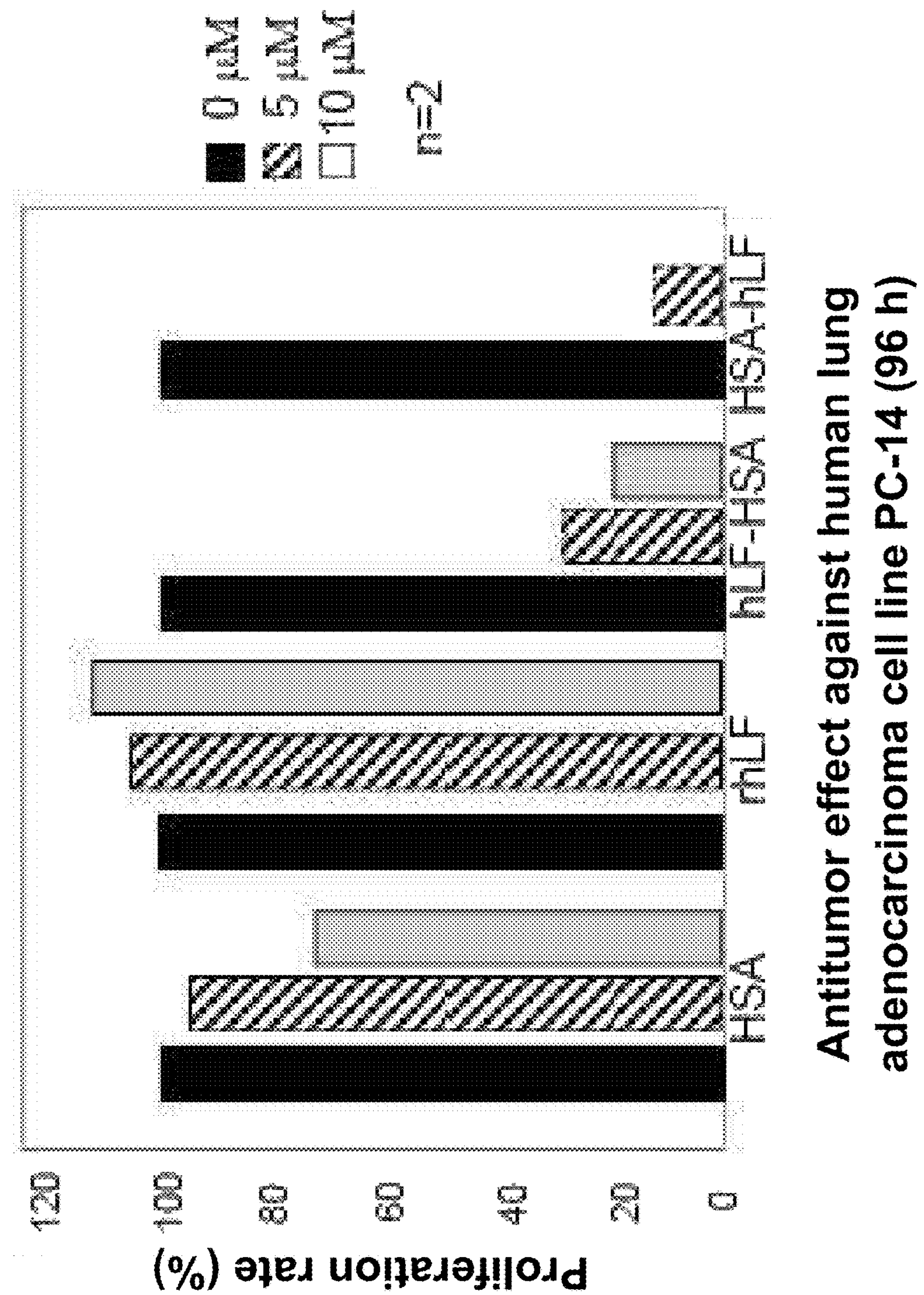
FIG. 14 shows the antitumor activity of hLF-HSA and HSA-hLF against human lung adenocarcinoma cells of poorly differentiated type.

Example 8: Antitumor Effect of the HSA Fusion Proteins Against Human Lung Adenocarcinoma Cells of Poorly Differentiated Type The human lung adenocarcinoma cell line PC-14 of poorly differentiated type was purchased from Immuno-Biological Laboratories Co., Ltd., Japan (IBL) and cultured in 10% FBS-supplemented RPMI-1640 (Wako Pure Chemical Industries, Ltd., Japan). In a 96-well cell culture plate, a 0.1% pig gelatin (Iwaki Glass Co. Ltd., Japan) solution was dispensed at 100 and the plate was allowed to stand for 1 hour to coat the plate with gelatin. PC-14 was suspended at $2.5\times10^4$ cells/ml in 10% FBS-supplemented RPMI-1640 medium, and the cells were seeded at 200 μl/well and cultured overnight at 37° C. under 5% $CO_2$. Using 10% FBS-supplemented RPMI-1640 (Wako Pure Chemical Industries, Ltd., Japan), rhLF, human serum albumin (HSA, Wako Pure Chemical Industries, Ltd., Japan) and the hLF-HSA and HSA-hLF fusion proteins were each prepared at 0, 5 and 10 μM (0 and 5 μM for HSA-hLF). After medium removal from the cells adhered to the plate, each protein solution thus prepared was added at 100 μl/well and the cells were cultured at 37° C. under 5% $CO_2$ for 96 hours. Subsequently, a Cell Counting Kit-8 (Dojindo Laboratories, Japan) was added to cause color development at 37° C. under 5% $CO_2$ for 2 hours. After color development, cell proliferation was evaluated by absorbance at 450 nm. Cell proliferation was expressed as a relative value (averaged from n=2) assuming that the absorbance of the medium containing no protein was set to 100% (FIG. 14). Slight inhibition of cell proliferation was observed in 10 μM HSA, whereas no inhibition of cell proliferation was observed in rhLF. On the other hand, the hLF-HSA and HSA-hLF fusion proteins were found to remarkably inhibit cell proliferation, and HSA-hLF particularly showed strong inhibition of cell proliferation when compared to hLF-HSA. The foregoing results indicated that the antitumor effect of hLF was enhanced upon HSA fusion.

Figure 15:
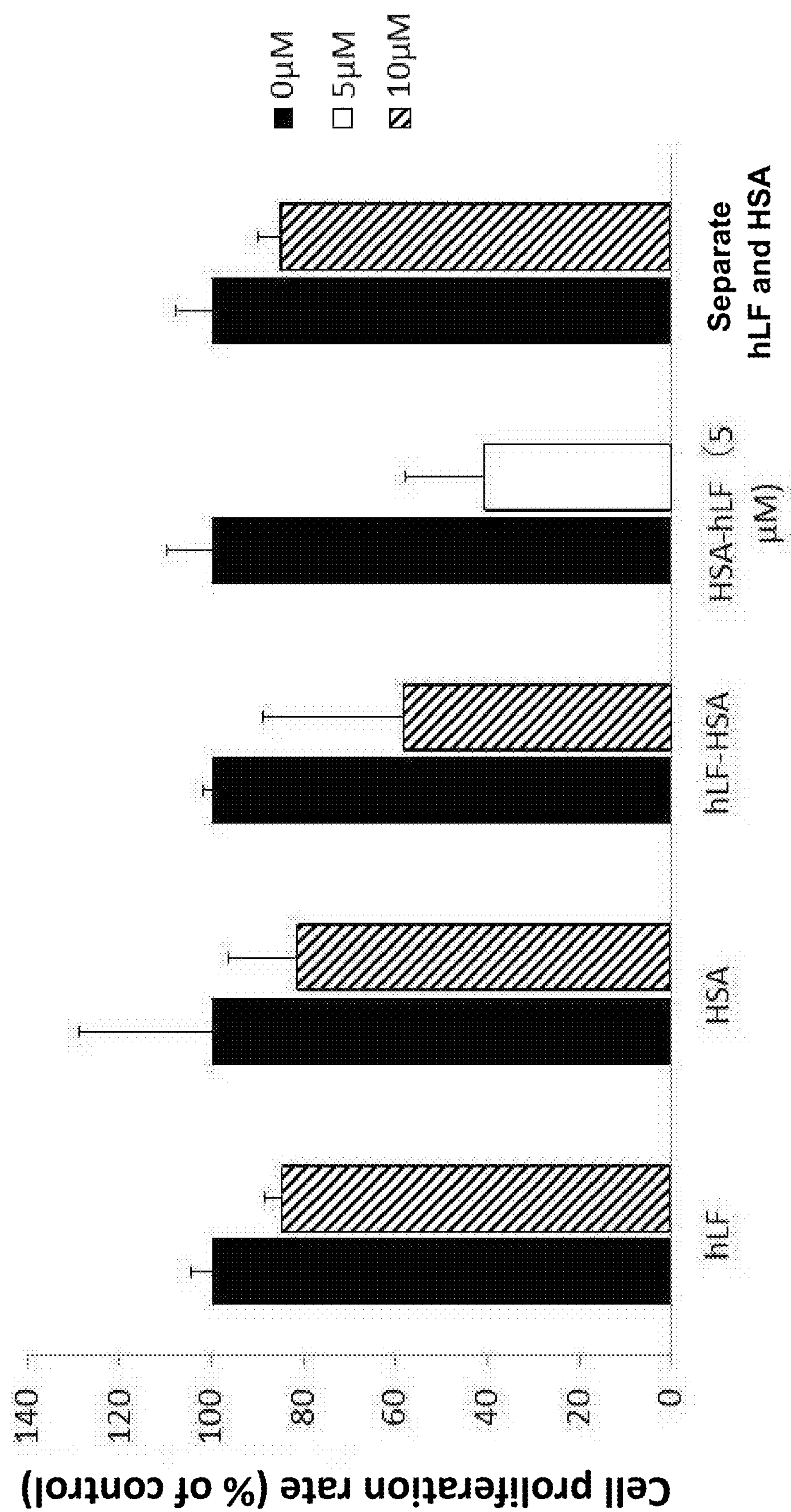
FIG. 15 shows the influence of covalent bonding in the fusion proteins on their antitumor effect.

Example 9: Influence of Covalent Bonding in the Fusion Proteins on their Antitumor Effect Next, to clarify whether HSA and rhLF are required to coexist for enhancement of this antitumor effect or both molecules are required to be fused by covalent bonding for this purpose, HSA and rhLF were both added to the same well at a concentration of 10 μM each, and the same procedure as shown in Example 8 was repeated to evaluate the proliferation of PC-14 cells, except that each protein was added to the cells and culture was continued for 72 hours, followed by color development for 2 hours with a Cell Counting Kit-8 (Dojindo Laboratories, Japan) in this experiment. Cell proliferation was expressed as a relative value (n=3, mean±standard deviation SD) assuming that the absorbance of the medium containing no protein was set to 100% (FIG. 15). In cases where 10 μM HSA alone was added and where 10 μM rhLF alone was added, slight inhibition of cell proliferation was observed. However, in a case where HSA and rhLF were both added to the same well at a concentration of 10 μM each, little inhibition of proliferation was observed, as in the cases of 10 μM HSA alone and 10 μM rhLF alone. On the other hand, in the case of the fusion proteins, hLF-HSA and HSA-hLF were both found to remarkably inhibit cell proliferation, and HSA-hLF particularly showed strong inhibition of cell proliferation when compared to hLF-HSA. This indicates that for enhancement of the antitumor effect of hLF, HSA is required to be fused with hLF by covalent bonding.

Figure 16:
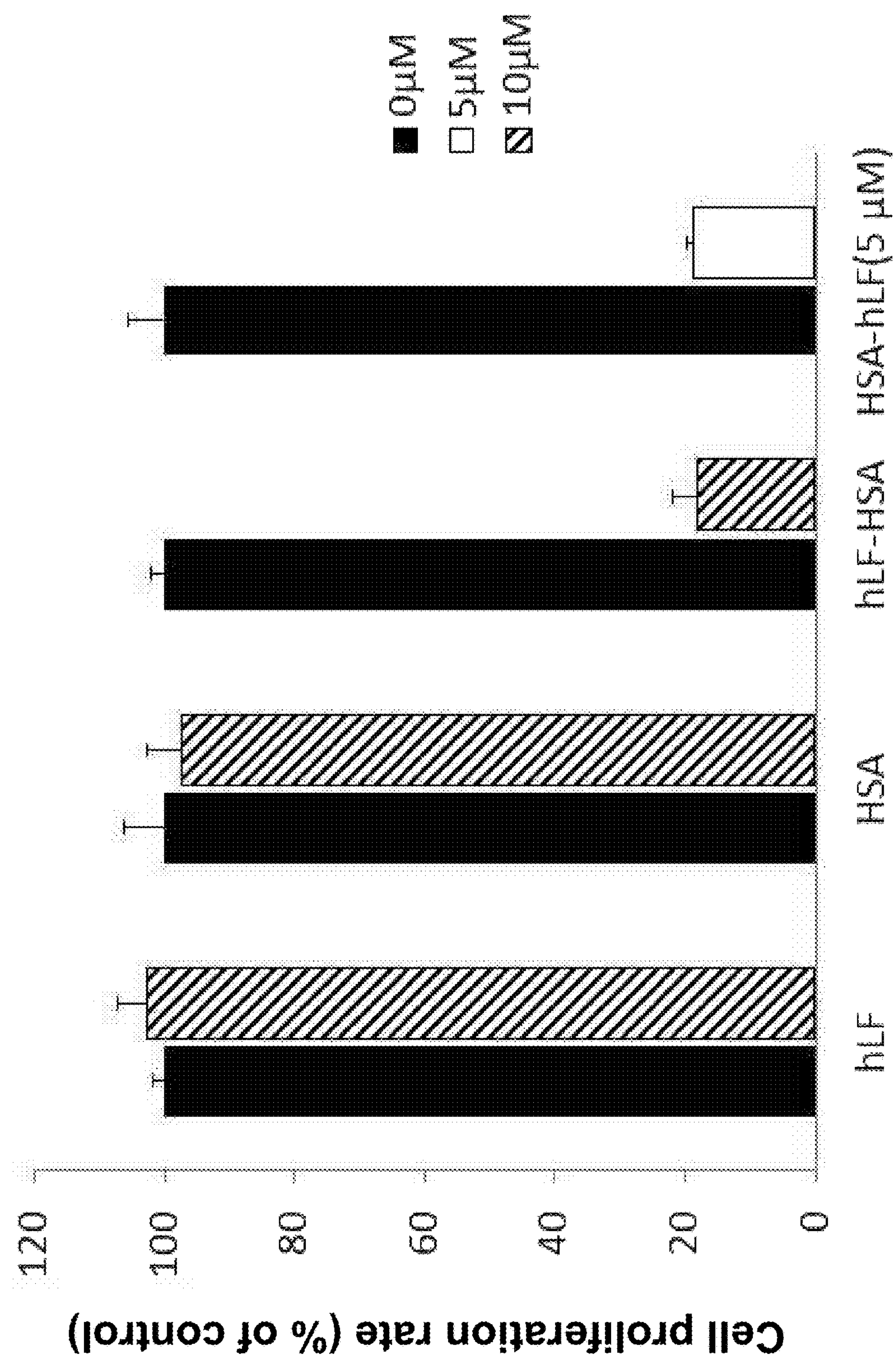
FIG. 16 shows the antitumor activity of hLF-HSA and HSA-hLF against human lung adenocarcinoma cells of differentiated type.

Example 10: Antitumor Effect of the HSA Fusion Proteins Against Human Lung Adenocarcinoma Cells of Differentiated Type The human lung adenocarcinoma cell line PC-9 of differentiated type was purchased from Immuno-Biological Laboratories Co., Ltd., Japan (IBL) and cultured in 10% FBS-supplemented RPMI-1640 (Wako Pure Chemical Industries, Ltd., Japan). In a 96-well cell culture plate, a 0.1% pig gelatin (Iwaki Glass Co. Ltd., Japan) solution was dispensed at 100 μl/well, and the plate was allowed to stand for 1 hour to coat the plate with gelatin. PC-9 was suspended at $2.5\times10^4$ cells/ml in 10% FBS-supplemented RPMI-1640 medium, and the cells were seeded at 200 μl/well and cultured overnight at 37° C. under 5% $CO_2$. Using 10% FBS-supplemented RPMI-1640 (Wako Pure Chemical Industries, Ltd., Japan), rhLF, human serum albumin (HSA, Wako Pure Chemical Industries, Ltd., Japan) and the hLF-HSA and HSA-hLF fusion proteins were each prepared at 0, 5 and 10 μM (0 and 5 μM for HSA-hLF). After medium removal from the cells adhered to the plate, each protein solution thus prepared was added at 100 μl/well, and the cells were cultured at 37° C. under 5% $CO_2$ for 72 hours. Subsequently, a Cell Counting Kit-8 (Dojindo Laboratories, Japan) was added to cause color development at 37° C. under 5% $CO_2$ for 2 hours. After color development, cell proliferation was evaluated by absorbance at 450 nm. Cell proliferation was expressed as a relative value (n=3, mean±standard deviation SD) assuming that the absorbance of the medium containing no protein was set to 100% (FIG. 16). No inhibition of cell proliferation was observed in 10 μM HSA and 10 μM rhLF. On the other hand, the hLF-HSA and HSA-hLF fusion proteins were found to remarkably inhibit cell proliferation, and HSA-hLF particularly showed strong inhibition of cell proliferation when compared to hLF-HSA. In view of the foregoing, the fusion proteins of the present invention were confirmed to also have an antitumor effect against human lung adenocarcinoma cells of differentiated type.

Example 11: Effect of the HSA Fusion Proteins on Human Lung Normal Cells

Figure 17:
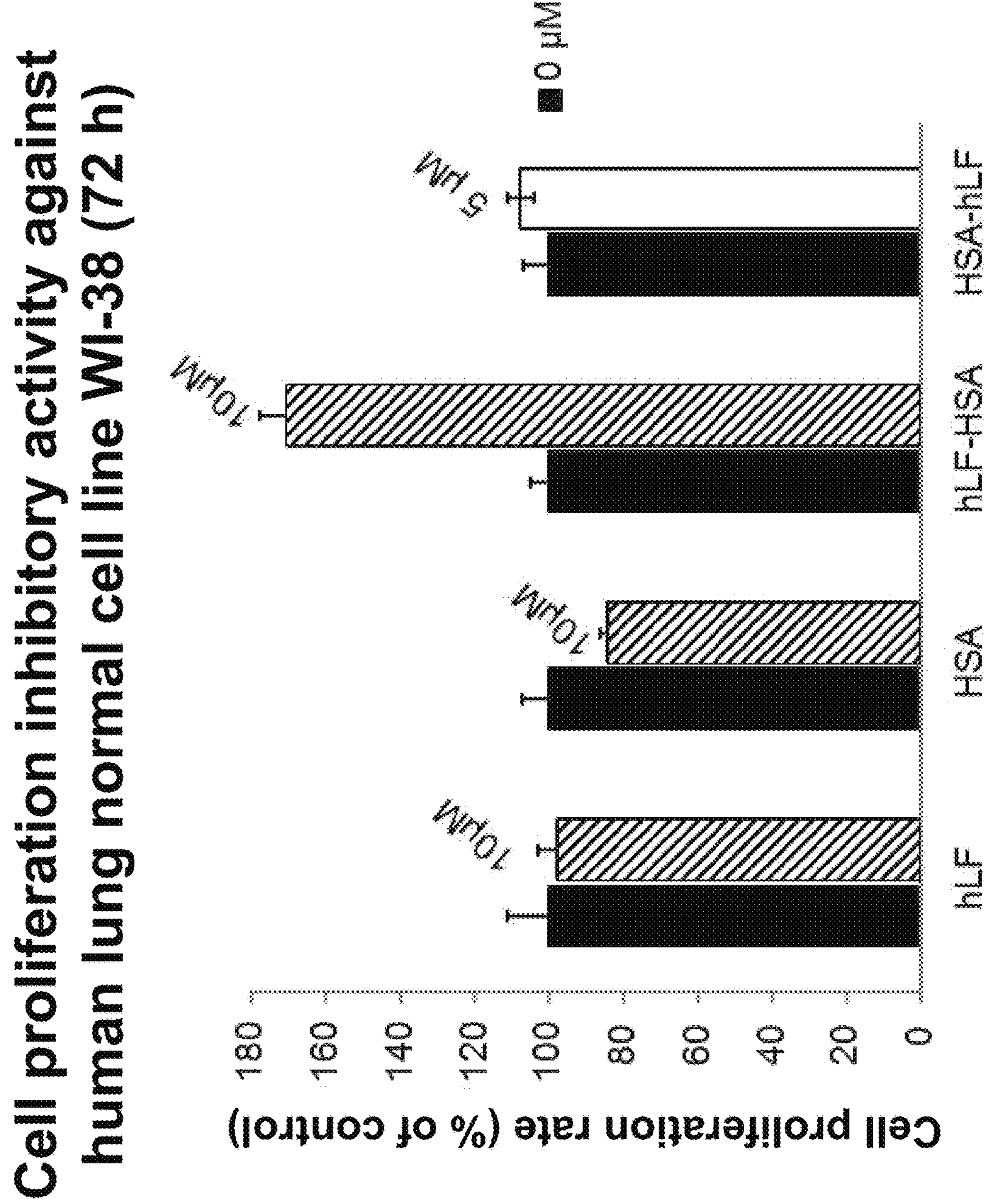
FIG. 17 shows the activity of hLF-HSA and HSA-hLF on human lung normal cells.

Next, the hLF-HSA and HSA-hLF fusion proteins were studied for their effect on the human lung normal cell line WI-38. WI-38 was purchased from JCRB Cell Bank and cultured in 10% FBS-supplemented D-MEM (low glucose) (Wako Pure Chemical Industries, Ltd., Japan). In a 96-well cell culture plate, a 0.1% pig gelatin (Iwaki Glass Co. Ltd., Japan) solution was dispensed at 100 μl/well, and the plate was allowed to stand for 1 hour to coat the plate with gelatin. WI-38 was suspended at $2.5\times10^4$ cells/ml in 10% FBS-supplemented D-MEM (low glucose) medium, and the cells were seeded at 200 μl/well and cultured overnight at 37° C. under 5% $CO_2$. Using 10% FBS-supplemented D-MEM (low glucose) (Wako Pure Chemical Industries, Ltd., Japan), protein solutions were prepared at 10 μM for rhLF, HSA and the hLF-HSA fusion protein and at 5 μM for HSA-hLF. After medium removal from the cells adhered to the plate, each protein solution thus prepared was added at 100 μl/well and the cells were cultured at 37° C. under 5% $CO_2$ for 72 hours. Subsequently, a Cell Counting Kit-8 (Dojindo Laboratories, Japan) was added to cause color development at 37° C. under 5% $CO_2$ for 2 hours. After color development, cell proliferation was evaluated by absorbance at 450 nm. Cell proliferation was expressed as a relative value (n=3, mean±standard deviation) assuming that the absorbance of the medium containing no protein was set to 100% (FIG. 17). Promotion of cell proliferation was observed in 10 μM hLF-HSA, whereas no inhibition of cell proliferation was observed in 10 μM rhLF, 10 μM HSA and 5 μM HSA-hLF. The foregoing results indicated that the antitumor effect of hLF was enhanced upon HSA fusion, and further that this antitumor effect was not shown on normal cells.

Thus, the fusion proteins of the present invention are shown to exert antitumor activity with no or little side effects if any.

INDUSTRIAL APPLICABILITY

The present invention provides a human lactoferrin (hLF)/human serum albumin (HSA) fusion protein with remarkably improved molecular stability. The present invention further provides a human lactoferrin (hLF)/human serum albumin (HSA) fusion protein which specifically exerts an antitumor effect against tumor cells, but not on normal cells.

The invention claimed is:

1. A fusion protein formed between:

(1) human serum albumin (HSA) or an HSA fragment consisting of an amino acid sequence that accounts for 90% or more of the amino acid sequence of HSA; and (2) human lactoferrin or a human lactoferrin fragment consisting of an amino acid sequence that accounts for 90% or more of the amino acid sequence of human lactoferrin, wherein the fusion protein is represented by:

(LF-*s*-Y)*n* or (Y-*s*-LF)*n*, and wherein LF represents human lactoferrin or the human lactoferrin fragment, Y represents human serum albumin or the HSA fragment, s represents any amino acid sequence of 0 to 10 residues, and n represents an integer of 1 to 10.

2. The fusion protein according to claim 1, which is represented by:

(LF-*s*-Y)*n*.

3. The fusion protein according to claim 1, which is represented by:

(Y-*s*-LF)*n*.

4. The fusion protein according to claim 1, wherein the fusion protein comprises the amino acid sequence of SEQ ID NO: 7.

5. The fusion protein according to claim 1, wherein the fusion protein comprises the amino acid sequence of SEQ ID NO: 14.

6. The fusion protein according to claim 1, wherein the fusion protein retains 50% or more of the iron-chelating ability of naturally occurring or recombinant human lactoferrin.

7. The fusion protein according to claim 1, wherein the fusion protein is capable of being taken up into cells via at least one receptor selected from the group consisting of: a lactoferrin receptor and an albumin receptor.

8. The fusion protein according to claim 1, wherein the fusion protein has improved pepsin resistance when compared to naturally occurring or recombinant human lactoferrin.

9. A nucleic acid molecule encoding the fusion protein according to claim 1.

10. An expression vector comprising the nucleic acid molecule according to claim 9.

11. A host cell comprising the expression vector according to claim 10.

12. A method of treating a disease ameliorated by the fusion protein according to claim 1, comprising administering the fusion protein to a patient in need thereof.

13. A pharmaceutical composition comprising the fusion protein according to claim 1 and a carrier.

14. A method of treating a tumor comprising administering the fusion protein according to claim 1 to a patient in need thereof.

15. The method according to claim 14, wherein the tumor is lung cancer.

16. A method of producing the fusion protein according to claim 1, comprising culturing a host cell comprising a gene encoding the fusion protein to express the fusion protein, and collecting the fusion protein from the host cell or the medium thereof.

17. The fusion protein according to claim 1, wherein LF represents human lactoferrin and Y represents human serum albumin.

* * * * *

SEQUENCE LISTING

```
<160> NUMBER OF SEQ ID NOS: 16

<210> SEQ ID NO 1
<211> LENGTH: 1830
<212> TYPE: DNA
<213> ORGANISM: Homo sapiens
<220> FEATURE:
<221> NAME/KEY: CDS
<222> LOCATION: (1)..(1830)

<400> SEQUENCE: 1

atg aag tgg gta acc ttt att tcc ctt ctt ttt ctc ttt agc tcg gct      48
Met Lys Trp Val Thr Phe Ile Ser Leu Leu Phe Leu Phe Ser Ser Ala
1               5                   10                  15

tat tcc agg ggt gtg ttt cgt cga gat gca cac aag agt gag gtt gct      96
Tyr Ser Arg Gly Val Phe Arg Arg Asp Ala His Lys Ser Glu Val Ala
            20                  25                  30

cat cgg ttt aaa gat ttg gga gaa gaa aat ttc aaa gcc ttg gtg ttg     144
His Arg Phe Lys Asp Leu Gly Glu Glu Asn Phe Lys Ala Leu Val Leu
        35                  40                  45

att gcc ttt gct cag tat ctt cag cag tgt cca ttt gaa gat cat gta     192
Ile Ala Phe Ala Gln Tyr Leu Gln Gln Cys Pro Phe Glu Asp His Val
    50                  55                  60

aaa tta gtg aat gaa gta act gaa ttt gca aaa aca tgt gtt gct gat     240
Lys Leu Val Asn Glu Val Thr Glu Phe Ala Lys Thr Cys Val Ala Asp
65                  70                  75                  80

gag tca gct gaa aat tgt gac aaa tca ctt cat acc ctt ttt gga gac     288
Glu Ser Ala Glu Asn Cys Asp Lys Ser Leu His Thr Leu Phe Gly Asp
                85                  90                  95

aaa tta tgc aca gtt gca act ctt cgt gaa acc tat ggt gaa atg gct     336
Lys Leu Cys Thr Val Ala Thr Leu Arg Glu Thr Tyr Gly Glu Met Ala
            100                 105                 110

gac tgc tgt gca aaa caa gaa cct gag aga aat gaa tgc ttc ttg caa     384
Asp Cys Cys Ala Lys Gln Glu Pro Glu Arg Asn Glu Cys Phe Leu Gln
        115                 120                 125

cac aaa gat gac aac cca aac ctc ccc cga ttg gtg aga cca gag gtt     432
His Lys Asp Asp Asn Pro Asn Leu Pro Arg Leu Val Arg Pro Glu Val
    130                 135                 140

gat gtg atg tgc act gct ttt cat gac aat gaa gag aca ttt ttg aaa     480
Asp Val Met Cys Thr Ala Phe His Asp Asn Glu Glu Thr Phe Leu Lys
145                 150                 155                 160

aaa tac tta tat gaa att gcc aga aga cat cct tac ttt tat gcc ccg     528
Lys Tyr Leu Tyr Glu Ile Ala Arg Arg His Pro Tyr Phe Tyr Ala Pro
                165                 170                 175

gaa ctc ctt ttc ttt gct aaa agg tat aaa gct gct ttt aca gaa tgt     576
Glu Leu Leu Phe Phe Ala Lys Arg Tyr Lys Ala Ala Phe Thr Glu Cys
            180                 185                 190

tgc caa gct gct gat aaa gct gcc tgc ctg ttg cca aag ctc gat gaa     624
Cys Gln Ala Ala Asp Lys Ala Ala Cys Leu Leu Pro Lys Leu Asp Glu
        195                 200                 205

ctt cgg gat gaa ggg aag gct tcg tct gcc aaa cag aga ctc aag tgt     672
Leu Arg Asp Glu Gly Lys Ala Ser Ser Ala Lys Gln Arg Leu Lys Cys
    210                 215                 220
```

```
gcc agt ctc caa aaa ttt gga gaa aga gct ttc aaa gca tgg gca gta      720
Ala Ser Leu Gln Lys Phe Gly Glu Arg Ala Phe Lys Ala Trp Ala Val
225                 230                 235                 240

gct cgc ctg agc cag aga ttt ccc aaa gct gag ttt gca gaa gtt tcc      768
Ala Arg Leu Ser Gln Arg Phe Pro Lys Ala Glu Phe Ala Glu Val Ser
                245                 250                 255

aag tta gtg aca gat ctt acc aaa gtc cac acg gaa tgc tgc cat gga      816
Lys Leu Val Thr Asp Leu Thr Lys Val His Thr Glu Cys Cys His Gly
            260                 265                 270

gat ctg ctt gaa tgt gct gat gac agg gcg gac ctt gcc aag tat atc      864
Asp Leu Leu Glu Cys Ala Asp Asp Arg Ala Asp Leu Ala Lys Tyr Ile
        275                 280                 285

tgt gaa aat caa gat tcg atc tcc agt aaa ctg aag gaa tgc tgt gaa      912
Cys Glu Asn Gln Asp Ser Ile Ser Ser Lys Leu Lys Glu Cys Cys Glu
    290                 295                 300

aaa cct ctg ttg gaa aaa tcc cac tgc att gcc gaa gtg gaa aat gat      960
Lys Pro Leu Leu Glu Lys Ser His Cys Ile Ala Glu Val Glu Asn Asp
305                 310                 315                 320

gag atg cct gct gac ttg cct tca tta gct gct gat ttt gtt gaa agt     1008
Glu Met Pro Ala Asp Leu Pro Ser Leu Ala Ala Asp Phe Val Glu Ser
                325                 330                 335

aag gat gtt tgc aaa aac tat gct gag gca aag gat gtc ttc ctg ggc     1056
Lys Asp Val Cys Lys Asn Tyr Ala Glu Ala Lys Asp Val Phe Leu Gly
            340                 345                 350

atg ttt ttg tat gaa tat gca aga agg cat cct gat tac tct gtc gtg     1104
Met Phe Leu Tyr Glu Tyr Ala Arg Arg His Pro Asp Tyr Ser Val Val
        355                 360                 365

ctg ctg ctg aga ctt gcc aag aca tat gaa acc act cta gag aag tgc     1152
Leu Leu Leu Arg Leu Ala Lys Thr Tyr Glu Thr Thr Leu Glu Lys Cys
    370                 375                 380

tgt gcc gct gca gat cct cat gaa tgc tat gcc aaa gtg ttc gat gaa     1200
Cys Ala Ala Ala Asp Pro His Glu Cys Tyr Ala Lys Val Phe Asp Glu
385                 390                 395                 400

ttt aaa cct ctt gtg gaa gag cct cag aat tta atc aaa caa aat tgt     1248
Phe Lys Pro Leu Val Glu Glu Pro Gln Asn Leu Ile Lys Gln Asn Cys
                405                 410                 415

gag ctt ttt gag cag ctt gga gag tac aaa ttc cag aat gcg cta tta     1296
Glu Leu Phe Glu Gln Leu Gly Glu Tyr Lys Phe Gln Asn Ala Leu Leu
            420                 425                 430

gtt cgt tac acc aag aaa gta ccc caa gtg tca act cca act ctt gta     1344
Val Arg Tyr Thr Lys Lys Val Pro Gln Val Ser Thr Pro Thr Leu Val
        435                 440                 445

gag gtc tca aga aac cta gga aaa gtg ggc agc aaa tgt tgt aaa cat     1392
Glu Val Ser Arg Asn Leu Gly Lys Val Gly Ser Lys Cys Cys Lys His
    450                 455                 460

cct gaa gca aaa aga atg ccc tgt gca gaa gac tat cta tcc gtg gtc     1440
Pro Glu Ala Lys Arg Met Pro Cys Ala Glu Asp Tyr Leu Ser Val Val
465                 470                 475                 480

ctg aac cag tta tgt gtg ttg cat gag aaa acg cca gta agt gac aga     1488
Leu Asn Gln Leu Cys Val Leu His Glu Lys Thr Pro Val Ser Asp Arg
                485                 490                 495

gtc acc aaa tgc tgc aca gaa tcc ttg gtg aac agg cga cca tgc ttt     1536
Val Thr Lys Cys Cys Thr Glu Ser Leu Val Asn Arg Arg Pro Cys Phe
            500                 505                 510

tca gct ctg gaa gtc gat gaa aca tac gtt ccc aaa gag ttt aat gct     1584
Ser Ala Leu Glu Val Asp Glu Thr Tyr Val Pro Lys Glu Phe Asn Ala
        515                 520                 525

gaa aca ttc acc ttc cat gca gat ata tgc aca ctt tct gag aag gag     1632
Glu Thr Phe Thr Phe His Ala Asp Ile Cys Thr Leu Ser Glu Lys Glu
```

```
    530                 535                 540

aga caa atc aag aaa caa act gca ctt gtt gag ctc gtg aaa cac aag      1680
Arg Gln Ile Lys Lys Gln Thr Ala Leu Val Glu Leu Val Lys His Lys
545                 550                 555                 560

ccc aag gca aca aaa gag caa ctg aaa gct gtt atg gat gat ttc gca      1728
Pro Lys Ala Thr Lys Glu Gln Leu Lys Ala Val Met Asp Asp Phe Ala
                565                 570                 575

gct ttt gta gag aag tgc tgc aag gct gac gat aag gag acc tgc ttt      1776
Ala Phe Val Glu Lys Cys Cys Lys Ala Asp Asp Lys Glu Thr Cys Phe
            580                 585                 590

gcc gag gag ggt aaa aaa ctt gtt gct gca agt caa gct gcc tta ggc      1824
Ala Glu Glu Gly Lys Lys Leu Val Ala Ala Ser Gln Ala Ala Leu Gly
        595                 600                 605

tta taa                                                              1830
Leu


<210> SEQ ID NO 2
<211> LENGTH: 609
<212> TYPE: PRT
<213> ORGANISM: Homo sapiens

<400> SEQUENCE: 2

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270
```

```
Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```

```
<210> SEQ ID NO 3
<211> LENGTH: 2136
<212> TYPE: DNA
<213> ORGANISM: Homo sapiens
<220> FEATURE:
<221> NAME/KEY: CDS
<222> LOCATION: (1)..(2136)

<400> SEQUENCE: 3

atg aaa ctt gtc ttc ctc gtc ctg ctg ttc ctc ggg gcc ctc gga ctg      48
Met Lys Leu Val Phe Leu Val Leu Leu Phe Leu Gly Ala Leu Gly Leu
```

-continued

```
1               5                   10                  15

tgt ctg gct ggc cgt agg aga agg agt gtt cag tgg tgc acc gta tcc       96
Cys Leu Ala Gly Arg Arg Arg Arg Ser Val Gln Trp Cys Thr Val Ser
            20                  25                  30

caa ccc gag gcc aca aaa tgc ttc caa tgg caa agg aat atg aga aga      144
Gln Pro Glu Ala Thr Lys Cys Phe Gln Trp Gln Arg Asn Met Arg Arg
        35                  40                  45

gtg cgt ggc cct cct gtc agc tgc ata aag aga gac tcc ccc atc cag      192
Val Arg Gly Pro Pro Val Ser Cys Ile Lys Arg Asp Ser Pro Ile Gln
    50                  55                  60

tgt atc cag gcc att gcg gaa aac agg gcc gat gct gtg acc ctt gat      240
Cys Ile Gln Ala Ile Ala Glu Asn Arg Ala Asp Ala Val Thr Leu Asp
65                  70                  75                  80

ggt ggt ttc ata tac gag gca ggc ctg gcc ccc tac aaa ctg cga cct      288
Gly Gly Phe Ile Tyr Glu Ala Gly Leu Ala Pro Tyr Lys Leu Arg Pro
                85                  90                  95

gta gcg gcg gaa gtc tac ggg acc gaa aga cag cca cga act cac tat      336
Val Ala Ala Glu Val Tyr Gly Thr Glu Arg Gln Pro Arg Thr His Tyr
            100                 105                 110

tat gcc gtg gct gtg gtg aag aag ggc ggc agc ttt cag ctg aac gaa      384
Tyr Ala Val Ala Val Val Lys Lys Gly Gly Ser Phe Gln Leu Asn Glu
        115                 120                 125

ctg caa ggt ctg aag tcc tgc cac aca ggc ctt cgc agg acc gct gga      432
Leu Gln Gly Leu Lys Ser Cys His Thr Gly Leu Arg Arg Thr Ala Gly
    130                 135                 140

tgg aat gtc cct ata ggg aca ctt cgt cca ttc ttg aat tgg acg ggt      480
Trp Asn Val Pro Ile Gly Thr Leu Arg Pro Phe Leu Asn Trp Thr Gly
145                 150                 155                 160

cca cct gag ccc att gag gca gct gtg gcc agg ttc ttc tca gcc agc      528
Pro Pro Glu Pro Ile Glu Ala Ala Val Ala Arg Phe Phe Ser Ala Ser
                165                 170                 175

tgt gtt ccc ggt gca gat aaa gga cag ttc ccc aac ctg tgt cgc ctg      576
Cys Val Pro Gly Ala Asp Lys Gly Gln Phe Pro Asn Leu Cys Arg Leu
            180                 185                 190

tgt gcg ggg aca ggg gaa aac aaa tgt gcc ttc tcc tcc cag gaa ccg      624
Cys Ala Gly Thr Gly Glu Asn Lys Cys Ala Phe Ser Ser Gln Glu Pro
        195                 200                 205

tac ttc agc tac tct ggt gcc ttc aag tgt ctg aga gac ggg gct gga      672
Tyr Phe Ser Tyr Ser Gly Ala Phe Lys Cys Leu Arg Asp Gly Ala Gly
    210                 215                 220

gac gtg gct ttt atc aga gag agc aca gtg ttt gag gac ctg tca gac      720
Asp Val Ala Phe Ile Arg Glu Ser Thr Val Phe Glu Asp Leu Ser Asp
225                 230                 235                 240

gag gct gaa agg gac gag tat gag tta ctc tgc cca gac aac act cgg      768
Glu Ala Glu Arg Asp Glu Tyr Glu Leu Leu Cys Pro Asp Asn Thr Arg
                245                 250                 255

aag cca gtg gac aag ttc aaa gac tgc cat ctg gcc cgg gtc cct tct      816
Lys Pro Val Asp Lys Phe Lys Asp Cys His Leu Ala Arg Val Pro Ser
            260                 265                 270

cat gcc gtt gtg gca cga agt gtg aat ggc aag gag gat gcc atc tgg      864
His Ala Val Val Ala Arg Ser Val Asn Gly Lys Glu Asp Ala Ile Trp
        275                 280                 285

aat ctt ctc cgc cag gca cag gaa aag ttt gga aag gac aag tca ccg      912
Asn Leu Leu Arg Gln Ala Gln Glu Lys Phe Gly Lys Asp Lys Ser Pro
    290                 295                 300

aaa ttc cag ctc ttt ggc tcc cct agt ggg cag aaa gat ctg ctg ttc      960
Lys Phe Gln Leu Phe Gly Ser Pro Ser Gly Gln Lys Asp Leu Leu Phe
305                 310                 315                 320

aag gac tct gcc att ggg ttt tcg agg gtg ccc ccg agg ata gat tct     1008
```

```
Lys Asp Ser Ala Ile Gly Phe Ser Arg Val Pro Pro Arg Ile Asp Ser
                325                 330                 335

ggg ctg tac ctt ggc tcc ggc tac ttc act gcc atc cag aac ttg agg      1056
Gly Leu Tyr Leu Gly Ser Gly Tyr Phe Thr Ala Ile Gln Asn Leu Arg
            340                 345                 350

aaa agt gag gag gaa gtg gct gcc cgg cgt gcg cgg gtc gtg tgg tgt      1104
Lys Ser Glu Glu Glu Val Ala Ala Arg Arg Ala Arg Val Val Trp Cys
        355                 360                 365

gcg gtg ggc gag cag gag ctg cgc aag tgt aac cag tgg agt ggc ttg      1152
Ala Val Gly Glu Gln Glu Leu Arg Lys Cys Asn Gln Trp Ser Gly Leu
    370                 375                 380

agc gaa ggc agc gtg acc tgc tcc tcg gcc tcc acc aca gag gac tgc      1200
Ser Glu Gly Ser Val Thr Cys Ser Ser Ala Ser Thr Thr Glu Asp Cys
385                 390                 395                 400

atc gcc ctg gtg ctg aaa gga gaa gct gat gcc atg agt ttg gat gga      1248
Ile Ala Leu Val Leu Lys Gly Glu Ala Asp Ala Met Ser Leu Asp Gly
                405                 410                 415

gga tat gtg tac act gca ggc aaa tgt ggt ttg gtg cct gtc ctg gca      1296
Gly Tyr Val Tyr Thr Ala Gly Lys Cys Gly Leu Val Pro Val Leu Ala
            420                 425                 430

gag aac tac aaa tcc caa caa agc agt gac cct gat cct aac tgt gtg      1344
Glu Asn Tyr Lys Ser Gln Gln Ser Ser Asp Pro Asp Pro Asn Cys Val
        435                 440                 445

gat aga cct gtg gaa gga tat ctt gct gtg gcg gtg gtt agg aga tca      1392
Asp Arg Pro Val Glu Gly Tyr Leu Ala Val Ala Val Val Arg Arg Ser
    450                 455                 460

gac act agc ctt acc tgg aac tct gtg aaa ggc aag aag tcc tgc cac      1440
Asp Thr Ser Leu Thr Trp Asn Ser Val Lys Gly Lys Lys Ser Cys His
465                 470                 475                 480

acc gcc gtg gac agg act gca ggc tgg aat atc ccc atg ggc ctg ctc      1488
Thr Ala Val Asp Arg Thr Ala Gly Trp Asn Ile Pro Met Gly Leu Leu
                485                 490                 495

ttc aac cag acg ggc tcc tgc aaa ttt gat gaa tat ttc agt caa agc      1536
Phe Asn Gln Thr Gly Ser Cys Lys Phe Asp Glu Tyr Phe Ser Gln Ser
            500                 505                 510

tgt gcc cct ggg tct gac ccg aga tct aat ctc tgt gct ctg tgt att      1584
Cys Ala Pro Gly Ser Asp Pro Arg Ser Asn Leu Cys Ala Leu Cys Ile
        515                 520                 525

ggc gac gag cag ggt gag aat aag tgc gtg ccc aac agc aat gag aga      1632
Gly Asp Glu Gln Gly Glu Asn Lys Cys Val Pro Asn Ser Asn Glu Arg
    530                 535                 540

tac tac ggc tac act ggg gct ttc cgg tgc ctg gct gag aat gct gga      1680
Tyr Tyr Gly Tyr Thr Gly Ala Phe Arg Cys Leu Ala Glu Asn Ala Gly
545                 550                 555                 560

gac gtt gca ttt gtg aaa gat gtc act gtc ttg cag aac act gat gga      1728
Asp Val Ala Phe Val Lys Asp Val Thr Val Leu Gln Asn Thr Asp Gly
                565                 570                 575

aat aac aat gac gca tgg gct aag gat ttg aag ctg gca gac ttt gcg      1776
Asn Asn Asn Asp Ala Trp Ala Lys Asp Leu Lys Leu Ala Asp Phe Ala
            580                 585                 590

ctg ctg tgc ctc gat ggc aaa cgg aag cct gtg act gag gct aga agc      1824
Leu Leu Cys Leu Asp Gly Lys Arg Lys Pro Val Thr Glu Ala Arg Ser
        595                 600                 605

tgc cat ctt gcc atg gcc ccg aat cat gcc gtg gtg tct cgg atg gat      1872
Cys His Leu Ala Met Ala Pro Asn His Ala Val Val Ser Arg Met Asp
    610                 615                 620

aag gtg gaa cgc ctg aaa cag gtg ttg ctc cac caa cag gct aaa ttt      1920
Lys Val Glu Arg Leu Lys Gln Val Leu Leu His Gln Gln Ala Lys Phe
625                 630                 635                 640
```

```
ggg aga aat gga tct gac tgc ccg gac aag ttt tgc tta ttc cag tct      1968
Gly Arg Asn Gly Ser Asp Cys Pro Asp Lys Phe Cys Leu Phe Gln Ser
                645                 650                 655

gaa acc aaa aac ctt ctg ttc aat gac aac act gag tgt ctg gcc aga      2016
Glu Thr Lys Asn Leu Leu Phe Asn Asp Asn Thr Glu Cys Leu Ala Arg
            660                 665                 670

ctc cat ggc aaa aca aca tat gaa aaa tat ttg gga cca cag tat gtc      2064
Leu His Gly Lys Thr Thr Tyr Glu Lys Tyr Leu Gly Pro Gln Tyr Val
        675                 680                 685

gca ggc att act aat ctg aaa aag tgc tca acc tcc ccc ctc ctg gaa      2112
Ala Gly Ile Thr Asn Leu Lys Lys Cys Ser Thr Ser Pro Leu Leu Glu
    690                 695                 700

gcc tgt gaa ttc ctc agg aag taa                                      2136
Ala Cys Glu Phe Leu Arg Lys
705                 710


<210> SEQ ID NO 4
<211> LENGTH: 711
<212> TYPE: PRT
<213> ORGANISM: Homo sapiens

<400> SEQUENCE: 4

Met Lys Leu Val Phe Leu Val Leu Leu Phe Leu Gly Ala Leu Gly Leu
1               5                   10                  15

Cys Leu Ala Gly Arg Arg Arg Arg Ser Val Gln Trp Cys Thr Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270
```

```
His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
        435                 440                 445

Asp Arg Pro Val Glu Gly Tyr Leu Ala Val Ala Val Val Arg Arg Ser
    450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Asp Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
```

690 695 700

Ala Cys Glu Phe Leu Arg Lys
705 710

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
cgcggatccc gatgcacaca agagtgaggt 30

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
aaggaaaaaa gcggccgctt ataagcctaa ggcagctt 38

<210> SEQ ID NO 7
<211> LENGTH: 1298
<212> TYPE: PRT
<213> ORGANISM: Artificial Sequence
<220> FEATURE:
<223> OTHER INFORMATION: hLF-HSA fusion protein

<400> SEQUENCE: 7

Met Lys Leu Val Phe Leu Val Leu Leu Phe Leu Gly Ala Leu Gly Leu
1 5 10 15

Cys Leu Ala Gly Arg Arg Arg Arg Ser Val Gln Trp Cys Ala Val Ser
20 25 30

Gln Pro Glu Ala Thr Lys Cys Phe Gln Trp Gln Arg Asn Met Arg Lys
35 40 45

Val Arg Gly Pro Pro Val Ser Cys Ile Lys Arg Asp Ser Pro Ile Gln
50 55 60

Cys Ile Gln Ala Ile Ala Glu Asn Arg Ala Asp Ala Val Thr Leu Asp
65 70 75 80

Gly Gly Phe Ile Tyr Glu Ala Gly Leu Ala Pro Tyr Lys Leu Arg Pro
85 90 95

Val Ala Ala Glu Val Tyr Gly Thr Glu Arg Gln Pro Arg Thr His Tyr
100 105 110

Tyr Ala Val Ala Val Val Lys Lys Gly Gly Ser Phe Gln Leu Asn Glu
115 120 125

Leu Gln Gly Leu Lys Ser Cys His Thr Gly Leu Arg Arg Thr Ala Gly
130 135 140

Trp Asn Val Pro Ile Gly Thr Leu Arg Pro Phe Leu Asn Trp Thr Gly
145 150 155 160

Pro Pro Glu Pro Ile Glu Ala Ala Val Ala Arg Phe Phe Ser Ala Ser
165 170 175

Cys Val Pro Gly Ala Asp Lys Gly Gln Phe Pro Asn Leu Cys Arg Leu
180 185 190

Cys Ala Gly Thr Gly Glu Asn Lys Cys Ala Phe Ser Ser Gln Glu Pro
195 200 205

Tyr Phe Ser Tyr Ser Gly Ala Phe Lys Cys Leu Arg Asp Gly Ala Gly

```
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
        435                 440                 445

Asp Arg Pro Val Glu Gly Tyr Leu Ala Val Ala Val Val Arg Arg Ser
    450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640
```

```
Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys Asp Pro Asp Ala His Lys Ser Glu Val
705                 710                 715                 720

Ala His Arg Phe Lys Asp Leu Gly Glu Glu Asn Phe Lys Ala Leu Val
                725                 730                 735

Leu Ile Ala Phe Ala Gln Tyr Leu Gln Gln Cys Pro Phe Glu Asp His
            740                 745                 750

Val Lys Leu Val Asn Glu Val Thr Glu Phe Ala Lys Thr Cys Val Ala
        755                 760                 765

Asp Glu Ser Ala Glu Asn Cys Asp Lys Ser Leu His Thr Leu Phe Gly
    770                 775                 780

Asp Lys Leu Cys Thr Val Ala Thr Leu Arg Glu Thr Tyr Gly Glu Met
785                 790                 795                 800

Ala Asp Cys Cys Ala Lys Gln Glu Pro Glu Arg Asn Glu Cys Phe Leu
                805                 810                 815

Gln His Lys Asp Asp Asn Pro Asn Leu Pro Arg Leu Val Arg Pro Glu
            820                 825                 830

Val Asp Val Met Cys Thr Ala Phe His Asp Asn Glu Glu Thr Phe Leu
        835                 840                 845

Lys Lys Tyr Leu Tyr Glu Ile Ala Arg Arg His Pro Tyr Phe Tyr Ala
    850                 855                 860

Pro Glu Leu Leu Phe Phe Ala Lys Arg Tyr Lys Ala Ala Phe Thr Glu
865                 870                 875                 880

Cys Cys Gln Ala Ala Asp Lys Ala Ala Cys Leu Leu Pro Lys Leu Asp
                885                 890                 895

Glu Leu Arg Asp Glu Gly Lys Ala Ser Ser Ala Lys Gln Arg Leu Lys
            900                 905                 910

Cys Ala Ser Leu Gln Lys Phe Gly Glu Arg Ala Phe Lys Ala Trp Ala
        915                 920                 925

Val Ala Arg Leu Ser Gln Arg Phe Pro Lys Ala Glu Phe Ala Glu Val
    930                 935                 940

Ser Lys Leu Val Thr Asp Leu Thr Lys Val His Thr Glu Cys Cys His
945                 950                 955                 960

Gly Asp Leu Leu Glu Cys Ala Asp Asp Arg Ala Asp Leu Ala Lys Tyr
                965                 970                 975

Ile Cys Glu Asn Gln Asp Ser Ile Ser Ser Lys Leu Lys Glu Cys Cys
            980                 985                 990

Glu Lys Pro Leu Leu Glu Lys Ser  His Cys Ile Ala Glu  Val Glu Asn
        995                 1000                1005

Asp Glu  Met Pro Ala Asp Leu  Pro Ser Leu Ala Ala  Asp Phe Val
    1010                1015                1020

Glu Ser  Lys Asp Val Cys Lys  Asn Tyr Ala Glu Ala  Lys Asp Val
    1025                1030                1035

Phe Leu  Gly Met Phe Leu Tyr  Glu Tyr Ala Arg Arg  His Pro Asp
    1040                1045                1050
```

Tyr Ser Val Val Leu Leu Leu Arg Leu Ala Lys Thr Tyr Glu Thr
1055 1060 1065

Thr Leu Glu Lys Cys Cys Ala Ala Ala Asp Pro His Glu Cys Tyr
1070 1075 1080

Ala Lys Val Phe Asp Glu Phe Lys Pro Leu Val Glu Glu Pro Gln
1085 1090 1095

Asn Leu Ile Lys Gln Asn Cys Glu Leu Phe Glu Gln Leu Gly Glu
1100 1105 1110

Tyr Lys Phe Gln Asn Ala Leu Leu Val Arg Tyr Thr Lys Lys Val
1115 1120 1125

Pro Gln Val Ser Thr Pro Thr Leu Val Glu Val Ser Arg Asn Leu
1130 1135 1140

Gly Lys Val Gly Ser Lys Cys Cys Lys His Pro Glu Ala Lys Arg
1145 1150 1155

Met Pro Cys Ala Glu Asp Tyr Leu Ser Val Val Leu Asn Gln Leu
1160 1165 1170

Cys Val Leu His Glu Lys Thr Pro Val Ser Asp Arg Val Thr Lys
1175 1180 1185

Cys Cys Thr Glu Ser Leu Val Asn Arg Arg Pro Cys Phe Ser Ala
1190 1195 1200

Leu Glu Val Asp Glu Thr Tyr Val Pro Lys Glu Phe Asn Ala Glu
1205 1210 1215

Thr Phe Thr Phe His Ala Asp Ile Cys Thr Leu Ser Glu Lys Glu
1220 1225 1230

Arg Gln Ile Lys Lys Gln Thr Ala Leu Val Glu Leu Val Lys His
1235 1240 1245

Lys Pro Lys Ala Thr Lys Glu Gln Leu Lys Ala Val Met Asp Asp
1250 1255 1260

Phe Ala Ala Phe Val Glu Lys Cys Cys Lys Ala Asp Asp Lys Glu
1265 1270 1275

Thr Cys Phe Ala Glu Glu Gly Lys Lys Leu Val Ala Ala Ser Gln
1280 1285 1290

Ala Ala Leu Gly Leu
1295

<210> SEQ ID NO 8
<211> LENGTH: 711
<212> TYPE: PRT
<213> ORGANISM: Artificial Sequence
<220> FEATURE:
<223> OTHER INFORMATION: hLF plus signal sequence

<400> SEQUENCE: 8

Met Lys Leu Val Phe Leu Val Leu Leu Phe Leu Gly Ala Leu Gly Leu
1 5 10 15

Cys Leu Ala Gly Arg Arg Arg Arg Ser Val Gln Trp Cys Ala Val Ser
20 25 30

Gln Pro Glu Ala Thr Lys Cys Phe Gln Trp Gln Arg Asn Met Arg Lys
35 40 45

Val Arg Gly Pro Pro Val Ser Cys Ile Lys Arg Asp Ser Pro Ile Gln
50 55 60

Cys Ile Gln Ala Ile Ala Glu Asn Arg Ala Asp Ala Val Thr Leu Asp
65 70 75 80

Gly Gly Phe Ile Tyr Glu Ala Gly Leu Ala Pro Tyr Lys Leu Arg Pro
85 90 95

-continued

```
Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
        435                 440                 445

Asp Arg Pro Val Glu Gly Tyr Leu Ala Val Ala Val Val Arg Arg Ser
    450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
```

```
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710


<210> SEQ ID NO 9
<211> LENGTH: 585
<212> TYPE: PRT
<213> ORGANISM: Artificial Sequence
<220> FEATURE:
<223> OTHER INFORMATION: HSA

<400> SEQUENCE: 9

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
```

-continued

```
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
cggaattcat gaagtgggta acctttat 28

<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11
ccgctcgagt aagcctaagg cagcttgac 29

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
ctcgagatgg gccgtagga 19

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gcggccgctt acttcctgag gaactcac 28

<210> SEQ ID NO 14
<211> LENGTH: 1304
<212> TYPE: PRT
<213> ORGANISM: Artificial Sequence
<220> FEATURE:
<223> OTHER INFORMATION: HSA-hLF fusion protein

<400> SEQUENCE: 14

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110
```

```
Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525
```

```
Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu Leu Glu Met Gly Arg Arg Arg Arg Ser Val Gln Trp Cys Ala Val
    610                 615                 620

Ser Gln Pro Glu Ala Thr Lys Cys Phe Gln Trp Gln Arg Asn Met Arg
625                 630                 635                 640

Lys Val Arg Gly Pro Pro Val Ser Cys Ile Lys Arg Asp Ser Pro Ile
                645                 650                 655

Gln Cys Ile Gln Ala Ile Ala Glu Asn Arg Ala Asp Ala Val Thr Leu
            660                 665                 670

Asp Gly Gly Phe Ile Tyr Glu Ala Gly Leu Ala Pro Tyr Lys Leu Arg
        675                 680                 685

Pro Val Ala Ala Glu Val Tyr Gly Thr Glu Arg Gln Pro Arg Thr His
    690                 695                 700

Tyr Tyr Ala Val Ala Val Val Lys Lys Gly Gly Ser Phe Gln Leu Asn
705                 710                 715                 720

Glu Leu Gln Gly Leu Lys Ser Cys His Thr Gly Leu Arg Arg Thr Ala
                725                 730                 735

Gly Trp Asn Val Pro Ile Gly Thr Leu Arg Pro Phe Leu Asn Trp Thr
            740                 745                 750

Gly Pro Pro Glu Pro Ile Glu Ala Ala Val Ala Arg Phe Phe Ser Ala
        755                 760                 765

Ser Cys Val Pro Gly Ala Asp Lys Gly Gln Phe Pro Asn Leu Cys Arg
    770                 775                 780

Leu Cys Ala Gly Thr Gly Glu Asn Lys Cys Ala Phe Ser Ser Gln Glu
785                 790                 795                 800

Pro Tyr Phe Ser Tyr Ser Gly Ala Phe Lys Cys Leu Arg Asp Gly Ala
                805                 810                 815

Gly Asp Val Ala Phe Ile Arg Glu Ser Thr Val Phe Glu Asp Leu Ser
            820                 825                 830

Asp Glu Ala Glu Arg Asp Glu Tyr Glu Leu Leu Cys Pro Asp Asn Thr
        835                 840                 845

Arg Lys Pro Val Asp Lys Phe Lys Asp Cys His Leu Ala Arg Val Pro
    850                 855                 860

Ser His Ala Val Val Ala Arg Ser Val Asn Gly Lys Glu Asp Ala Ile
865                 870                 875                 880

Trp Asn Leu Leu Arg Gln Ala Gln Glu Lys Phe Gly Lys Asp Lys Ser
                885                 890                 895

Pro Lys Phe Gln Leu Phe Gly Ser Pro Ser Gly Gln Lys Asp Leu Leu
            900                 905                 910

Phe Lys Asp Ser Ala Ile Gly Phe Ser Arg Val Pro Pro Arg Ile Asp
        915                 920                 925

Ser Gly Leu Tyr Leu Gly Ser Gly Tyr Phe Thr Ala Ile Gln Asn Leu
    930                 935                 940

Arg Lys Ser Glu Glu Glu Val Ala Ala Arg Arg Ala Arg Val Val Trp
```

```
945                 950                 955                 960

Cys Ala Val Gly Glu Gln Glu Leu Arg Lys Cys Asn Gln Trp Ser Gly
                965                 970                 975

Leu Ser Glu Gly Ser Val Thr Cys Ser Ser Ala Ser Thr Thr Glu Asp
            980                 985                 990

Cys Ile Ala Leu Val Leu Lys Gly  Glu Ala Asp Ala Met  Ser Leu Asp
        995                 1000                1005

Gly Gly  Tyr Val Tyr Thr Ala  Gly Lys Cys Gly Leu  Val Pro Val
    1010                 1015                1020

Leu Ala  Glu Asn Tyr Lys Ser  Gln Gln Ser Ser Asp  Pro Asp Pro
    1025                 1030                1035

Asn Cys  Val Asp Arg Pro Val  Glu Gly Tyr Leu Ala  Val Ala Val
    1040                 1045                1050

Val Arg  Arg Ser Asp Thr Ser  Leu Thr Trp Asn Ser  Val Lys Gly
    1055                 1060                1065

Lys Lys  Ser Cys His Thr Ala  Val Asp Arg Thr Ala  Gly Trp Asn
    1070                 1075                1080

Ile Pro  Met Gly Leu Leu Phe  Asn Gln Thr Gly Ser  Cys Lys Phe
    1085                 1090                1095

Asp Glu  Tyr Phe Ser Gln Ser  Cys Ala Pro Gly Ser  Asp Pro Arg
    1100                 1105                1110

Ser Asn  Leu Cys Ala Leu Cys  Ile Gly Asp Glu Gln  Gly Glu Asn
    1115                 1120                1125

Lys Cys  Val Pro Asn Ser Asn  Glu Arg Tyr Tyr Gly  Tyr Thr Gly
    1130                 1135                1140

Ala Phe  Arg Cys Leu Ala Glu  Asn Ala Gly Asp Val  Ala Phe Val
    1145                 1150                1155

Lys Asp  Val Thr Val Leu Gln  Asn Thr Asp Gly Asn  Asn Asn Glu
    1160                 1165                1170

Ala Trp  Ala Lys Asp Leu Lys  Leu Ala Asp Phe Ala  Leu Leu Cys
    1175                 1180                1185

Leu Asp  Gly Lys Arg Lys Pro  Val Thr Glu Ala Arg  Ser Cys His
    1190                 1195                1200

Leu Ala  Met Ala Pro Asn His  Ala Val Val Ser Arg  Met Asp Lys
    1205                 1210                1215

Val Glu  Arg Leu Lys Gln Val  Leu Leu His Gln Gln  Ala Lys Phe
    1220                 1225                1230

Gly Arg  Asn Gly Ser Asp Cys  Pro Asp Lys Phe Cys  Leu Phe Gln
    1235                 1240                1245

Ser Glu  Thr Lys Asn Leu Leu  Phe Asn Asp Asn Thr  Glu Cys Leu
    1250                 1255                1260

Ala Arg  Leu His Gly Lys Thr  Thr Tyr Glu Lys Tyr  Leu Gly Pro
    1265                 1270                1275

Gln Tyr  Val Ala Gly Ile Thr  Asn Leu Lys Lys Cys  Ser Thr Ser
    1280                 1285                1290

Pro Leu  Leu Glu Ala Cys Glu  Phe Leu Arg Lys
    1295                 1300
```

<210> SEQ ID NO 15
<211> LENGTH: 609
<212> TYPE: PRT
<213> ORGANISM: Artificial Sequence
<220> FEATURE:
<223> OTHER INFORMATION: HSA plus signal sequence

```
<400> SEQUENCE: 15

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415
```

```
Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu


<210> SEQ ID NO 16
<211> LENGTH: 692
<212> TYPE: PRT
<213> ORGANISM: Artificial Sequence
<220> FEATURE:
<223> OTHER INFORMATION: hLF

<400> SEQUENCE: 16

Gly Arg Arg Arg Arg Ser Val Gln Trp Cys Ala Val Ser Gln Pro Glu
1               5                   10                  15

Ala Thr Lys Cys Phe Gln Trp Gln Arg Asn Met Arg Lys Val Arg Gly
            20                  25                  30

Pro Pro Val Ser Cys Ile Lys Arg Asp Ser Pro Ile Gln Cys Ile Gln
        35                  40                  45

Ala Ile Ala Glu Asn Arg Ala Asp Ala Val Thr Leu Asp Gly Gly Phe
    50                  55                  60

Ile Tyr Glu Ala Gly Leu Ala Pro Tyr Lys Leu Arg Pro Val Ala Ala
65                  70                  75                  80

Glu Val Tyr Gly Thr Glu Arg Gln Pro Arg Thr His Tyr Tyr Ala Val
                85                  90                  95

Ala Val Val Lys Lys Gly Gly Ser Phe Gln Leu Asn Glu Leu Gln Gly
            100                 105                 110

Leu Lys Ser Cys His Thr Gly Leu Arg Arg Thr Ala Gly Trp Asn Val
        115                 120                 125

Pro Ile Gly Thr Leu Arg Pro Phe Leu Asn Trp Thr Gly Pro Pro Glu
    130                 135                 140

Pro Ile Glu Ala Ala Val Ala Arg Phe Phe Ser Ala Ser Cys Val Pro
145                 150                 155                 160
```

```
Gly Ala Asp Lys Gly Gln Phe Pro Asn Leu Cys Arg Leu Cys Ala Gly
                165                 170                 175

Thr Gly Glu Asn Lys Cys Ala Phe Ser Ser Gln Glu Pro Tyr Phe Ser
            180                 185                 190

Tyr Ser Gly Ala Phe Lys Cys Leu Arg Asp Gly Ala Gly Asp Val Ala
        195                 200                 205

Phe Ile Arg Glu Ser Thr Val Phe Glu Asp Leu Ser Asp Glu Ala Glu
    210                 215                 220

Arg Asp Glu Tyr Glu Leu Leu Cys Pro Asp Asn Thr Arg Lys Pro Val
225                 230                 235                 240

Asp Lys Phe Lys Asp Cys His Leu Ala Arg Val Pro Ser His Ala Val
                245                 250                 255

Val Ala Arg Ser Val Asn Gly Lys Glu Asp Ala Ile Trp Asn Leu Leu
            260                 265                 270

Arg Gln Ala Gln Glu Lys Phe Gly Lys Asp Lys Ser Pro Lys Phe Gln
        275                 280                 285

Leu Phe Gly Ser Pro Ser Gly Gln Lys Asp Leu Leu Phe Lys Asp Ser
    290                 295                 300

Ala Ile Gly Phe Ser Arg Val Pro Pro Arg Ile Asp Ser Gly Leu Tyr
305                 310                 315                 320

Leu Gly Ser Gly Tyr Phe Thr Ala Ile Gln Asn Leu Arg Lys Ser Glu
                325                 330                 335

Glu Glu Val Ala Ala Arg Arg Ala Arg Val Val Trp Cys Ala Val Gly
            340                 345                 350

Glu Gln Glu Leu Arg Lys Cys Asn Gln Trp Ser Gly Leu Ser Glu Gly
        355                 360                 365

Ser Val Thr Cys Ser Ser Ala Ser Thr Thr Glu Asp Cys Ile Ala Leu
    370                 375                 380

Val Leu Lys Gly Glu Ala Asp Ala Met Ser Leu Asp Gly Gly Tyr Val
385                 390                 395                 400

Tyr Thr Ala Gly Lys Cys Gly Leu Val Pro Val Leu Ala Glu Asn Tyr
                405                 410                 415

Lys Ser Gln Gln Ser Ser Asp Pro Asp Pro Asn Cys Val Asp Arg Pro
            420                 425                 430

Val Glu Gly Tyr Leu Ala Val Ala Val Val Arg Arg Ser Asp Thr Ser
        435                 440                 445

Leu Thr Trp Asn Ser Val Lys Gly Lys Lys Ser Cys His Thr Ala Val
    450                 455                 460

Asp Arg Thr Ala Gly Trp Asn Ile Pro Met Gly Leu Leu Phe Asn Gln
465                 470                 475                 480

Thr Gly Ser Cys Lys Phe Asp Glu Tyr Phe Ser Gln Ser Cys Ala Pro
                485                 490                 495

Gly Ser Asp Pro Arg Ser Asn Leu Cys Ala Leu Cys Ile Gly Asp Glu
            500                 505                 510

Gln Gly Glu Asn Lys Cys Val Pro Asn Ser Asn Glu Arg Tyr Tyr Gly
        515                 520                 525

Tyr Thr Gly Ala Phe Arg Cys Leu Ala Glu Asn Ala Gly Asp Val Ala
    530                 535                 540

Phe Val Lys Asp Val Thr Val Leu Gln Asn Thr Asp Gly Asn Asn Asn
545                 550                 555                 560

Glu Ala Trp Ala Lys Asp Leu Lys Leu Ala Asp Phe Ala Leu Leu Cys
                565                 570                 575

Leu Asp Gly Lys Arg Lys Pro Val Thr Glu Ala Arg Ser Cys His Leu
```

-continued

```
            580                 585                 590

Ala Met Ala Pro Asn His Ala Val Val Ser Arg Met Asp Lys Val Glu
        595                 600                 605

Arg Leu Lys Gln Val Leu Leu His Gln Gln Ala Lys Phe Gly Arg Asn
    610                 615                 620

Gly Ser Asp Cys Pro Asp Lys Phe Cys Leu Phe Gln Ser Glu Thr Lys
625                 630                 635                 640

Asn Leu Leu Phe Asn Asp Asn Thr Glu Cys Leu Ala Arg Leu His Gly
                645                 650                 655

Lys Thr Thr Tyr Glu Lys Tyr Leu Gly Pro Gln Tyr Val Ala Gly Ile
            660                 665                 670

Thr Asn Leu Lys Lys Cys Ser Thr Ser Pro Leu Leu Glu Ala Cys Glu
        675                 680                 685

Phe Leu Arg Lys
    690
```